(12) United States Patent
Khaderi

(10) Patent No.: US 9,538,912 B2
(45) Date of Patent: *Jan. 10, 2017

(54) METHOD AND SYSTEM OF ENHANCING GANGLION CELL FUNCTION TO IMPROVE PHYSICAL PERFORMANCE

(76) Inventor: Syed Khizer Rahim Khaderi, Buena Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/595,930

(22) Filed: Aug. 27, 2012

(65) Prior Publication Data

US 2012/0322588 A1 Dec. 20, 2012

Related U.S. Application Data

(63) Continuation of application No. 12/353,941, filed on Jan. 14, 2009, now Pat. No. 8,251,508.

(60) Provisional application No. 61/020,953, filed on Jan. 14, 2008.

(51) Int. Cl.
*A61B 3/10* (2006.01)
*A61B 3/02* (2006.01)
*A61B 3/024* (2006.01)

(52) U.S. Cl.
CPC .................................. *A61B 3/024* (2013.01)

(58) Field of Classification Search
USPC .................................................. 351/200–246
See application file for complete search history.

(56) References Cited

U.S. PATENT DOCUMENTS

| | | | |
|---|---|---|---|
| 7,211,050 B1* | 5/2007 | Caplygin | 600/558 |
| 7,367,673 B2* | 5/2008 | McGrath et al. | 351/209 |
| 8,075,136 B2* | 12/2011 | Newman | 351/205 |
| 8,251,508 B2* | 8/2012 | Khaderi | 351/205 |
| 2007/0166675 A1 | 7/2007 | Atkins et al. | |

OTHER PUBLICATIONS

International Preliminary Report on Patentability mailed Jul. 29, 2010, for PCT Application No. PCT/US2009/31024 filed Jan. 14, 2009, 6 pages.
International Search Report mailed Jun. 30, 2009, for PCT Application No. PCT/US2009/31024 filed Jan. 14, 2009, 2 pages.

* cited by examiner

*Primary Examiner* — Mohammed Hasan
(74) *Attorney, Agent, or Firm* — Novel IP

(57) ABSTRACT

A method and a system of enhancing ganglion cell function using a gaming environment corresponding to a physical activity. The method and system may be used to implement one or more processes to improve a person's visual processing profile. In particular, the method and system may be used to improve a player's skill in the corresponding physical activity.

20 Claims, 21 Drawing Sheets

METHOD AND SYSTEM OF ENHANCING GANGLION CELL FUNCTION TO IMPROVE PHYSICAL PERFORMANCE

CROSS REFERENCE TO RELATED APPLICATION

This application is a continuation of U.S. patent application Ser. No. 12/353,941 (Now U.S. Pat. No. 8,251,508), filed Jan. 14, 2009, which claims the benefit of U.S. Provisional Application Ser. No. 61/020,953, filed Jan. 14, 2008, each of which is hereby incorporated by reference in its entirety.

TECHNICAL FIELD

The following disclosure relates to a system and method of developing a visual processing profile based on a retino-geniculo-cortical pathway.

BACKGROUND

The structures of the human eye transmit an image to the retina based on photons absorbed from the visual field. The retina contains five different cell types, organized in laminar fashion. At the back of the retina, furthest from the cornea, are a plurality of photoreceptors that convert light into electrochemical signals. Photoreceptors exist in two varieties: rod photoreceptors and cone photoreceptors. Rod photoreceptors have a long, cylindrically shaped outer segment with membranous disks that are stacked with photopigment. Cone cells have a shorter, more tapered outer segment with fewer membranous disks. The rods are much more sensitive to light than cones and mediate most vision at night or in low light. In contrast, the cones are differentially sensitive to varying wavelengths, and mediate color vision.

The electrochemical signals are relayed from the photoreceptors through the bipolar cells to the ganglion cells. The ganglion cells gather information and send it to the brain through the optic nerve. The innermost layer is the ganglion cell layer, which is the location of the ganglion cell bodies. The inner nuclear layer contains the cell bodies of the bipolar, amacrine and horizontal cells and the outer nuclear layer contains the cell bodies of the photoreceptors. The inner plexiform layer contains the connections between the bipolar, amacrine and ganglion cells. The outer plexiform layer contains the connections between the photoreceptors, horizontal cells and bipolar cells. The outer segments of the photoreceptor cells border on the pigmented epithelium, which absorbs excess light at the back of the retina.

Just like the rods and cones, whose structure and function are oriented entirely toward converting light energy into nerve impulses, every other type of cell in the retina is located and connected to perform some initial step in the processing of visual information.

While the other neurons in the retina emit only graduated electrical potentials, the ganglion cells are the only ones that send out neural signals in the form of action potentials. When it is considered that it is the ganglion cells' axons that form the optic nerve and thereby transmit information from the retina over large distances, the significance of the generation of action potentials in these cells becomes apparent. These potentials are generated spontaneously; and it is the frequency at which they are discharged that is increased or decreased by the appearance of light in these cells' receptive fields.

Though most ganglion cells have either ON-centre OFF-surround receptive fields or the reverse, there are other criteria that define other categories. On the basis of overall appearance, neural connections, and electrophysiological traits, at least three such categories of ganglion cells have been distinguished in retinas. However it is believed that at least eighteen different categories of ganglion cells exist in a human retina.

Intermediate cells such as bipolar cells, amacrine cells and horizontal cells convey the information received by the photoreceptors to neurons called ganglion cells. The human eye contains about 1.2 to 1.5 million retinal ganglion cells. As discussed above, there are three major types (subtypes) or categories of ganglion cells classified by their structure and function. These cells, the magnocellular cells (m-cells), parvocellular cells (p-cells) and koniocellular cells (k-cells) each having a unique role in visual processing.

The small parvocellular (or "p-cells") ganglion cells (from the Latin parvus, meaning "small") represent about 90% of the total population of ganglion cells. Large magnocellular (or "m-type") ganglion cells (from the Latin magnus, meaning "large") account for about 5%. Non-m, non-p ganglion cells, which have not yet been well characterized, account for the remaining 5%. These non-m, non-p cells include k-cells.

M-cells receive signals from a large number of photoreceptor cells. They have fast conduction velocities resulting in quick propagation of nerve impulses over a relatively large receptive field. The m-cells process images with low spatial resolution, but a fast temporal resolution. Furthermore, the m-cells demonstrate association with regions of the brain responsible for motion perception. Although these cells are sensitive to contrast stimulus, they show only weak response to chromatic input.

In contrast, the p-cells are responsible for the processing and visualization of color stimulus. They are generally involved in processing images at a lower conduction velocity and have a smaller receptive field responding to a small number of photoreceptor cells. Particularly, the p-cells show red-green color opponency having responses consistent with the interaction between medium-wavelength-sensitive (M or "green") and long-wavelength-sensitive (L or "red") photoreceptor cone cells. The p-cells show sustained response to stimuli and, opposite the m-cells, process images with high spatial resolution and slowed temporal resolution. The p-cells show association with areas of the brain relating to visual acuity and color perception.

The most commonly accepted theory is that m-cells are particularly involved in detecting movement in a stimulus, whereas p-cells, with their small receptive fields, would be more sensitive to its shape and details.

Cells belonging to the koniocellular ganglion pathway have a large visual field and show blue-yellow color opponency. K-cells show responses consistent with excitation from the short-wavelength-sensitive (S or "blue") and opponent input from a mixture of M and L cones. These "blue-on" cells are thought to derive opponent cone inputs through depolarizing and hyperpolarizing pathways.

Another distinction is essential for color detection: most p-cells and some non-m non-p cells are sensitive to differences in the wavelengths of light. Most p-cells are in fact "single color opponent cells," which means that the response to a given wavelength at the centre of their receptive fields is inhibited by the response to another wavelength in the surround. In the case of a cell with a red ON-centre and a green OFF-surround, red cones occupy the centre of the field and green cones occupy the surround. The same thing goes for cells with blue-yellow opposition, in which blue cones are opposed to red and green ones. Type M ganglion cells do not have any color opposition, simply because both the centre and the surround simultaneously receive information from more than one type of cone. Also, there are no m-cells in the fovea, which confirms that these cells do not play a role in processing color.

Various methods for determining the function of specific retinal ganglion cell types are known in the art. Current diagnostic tools and methods center on comparison of an individual to population norms to identify disease processes and stabilizing visual acuity based on these norms as well as coordination and timing of vision with bodily movements. However, these diagnostics and methods fail to address the visual processing of an individual as a ratio of retinal ganglion cell function. Furthermore, a correlation between the ratio or level of retinal ganglion function and high visual performance has not been thoroughly explained. Thus, there is a need in the art to determine and alter the ratio of function in the various retinal ganglion cells.

SUMMARY

In a game embodiment corresponding to a physical activity, such as baseball, a system may be used to implement one or more of the described processes to improve a person's visual processing profile. In particular, the game embodiment may be used to improve a player's skill in the corresponding physical activity.

DETAILED DESCRIPTION

The present disclosure describes a method of improving a visual processing profile for a person. The method may be performed on a single system that incorporates a number of separate components or on a distributed system which separates a portion of the measuring, computing, and storing components across a network. One example of such a network is described below.

Figure 1:
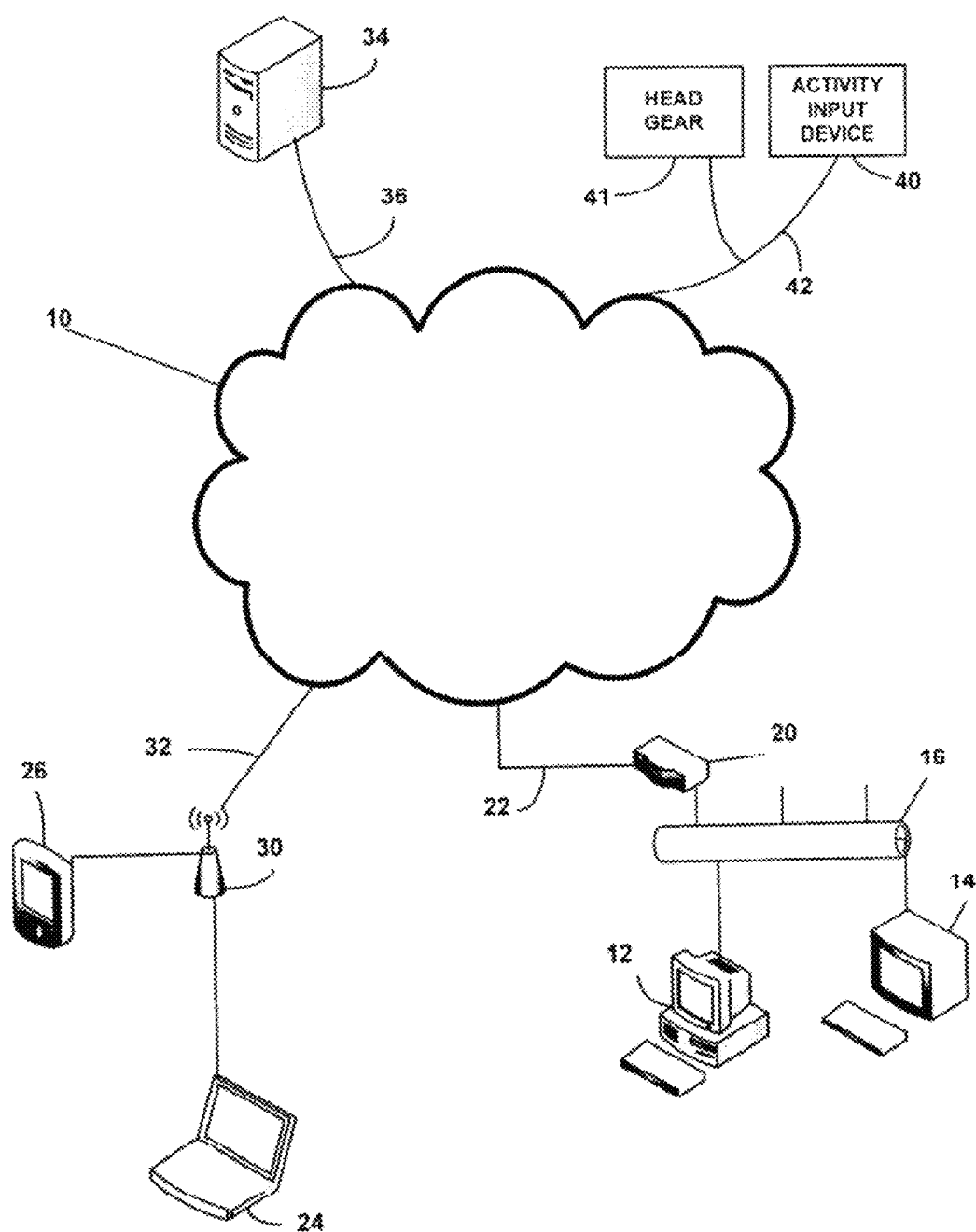
FIG. 1 is a diagram of one example of a network and network devices.

FIG. 1 illustrates an example of a network typical of the World Wide Web. A network 10 may be a virtual private network (VPN), or any other network that allows one or more computers, communication devices, databases, etc., to be communicatively connected to each other. The network 10 may be connected to a PC 12 and a computer terminal and monitor 14 via an Ethernet 16 and a router 20, and a land line 22. The network 10 may also be wirelessly connected to a laptop computer 24 and a personal data assistant 26 via a wireless communication station 30 and a wireless link 32. Similarly, a server 34 may be connected to the network 10 using a communication link 36.

Also, an activity input device 40 for measuring motion associated with physical activity of a user and a headset 41 for generating images and/or sounds for the user may be connected to the network 10 using another communication link 42. These components may alternatively be coupled to the network 10 via the wireless communication station 30 and the wireless link 32. Where the network 10 includes the Internet, data communication may take place over the network 10 via an Internet communication protocol. In operation, the client PC 12 may view or request data from any other computing device connected to the network 10. Further, the PC 12 may send data to any other computing device connected to the network 10. It is noted that each of the components listed above may be general purpose components or specially designed components for developing a visual processing profile for a person and enhancing a retino-geniculo-cortical pathway for the person.

Figure 2:
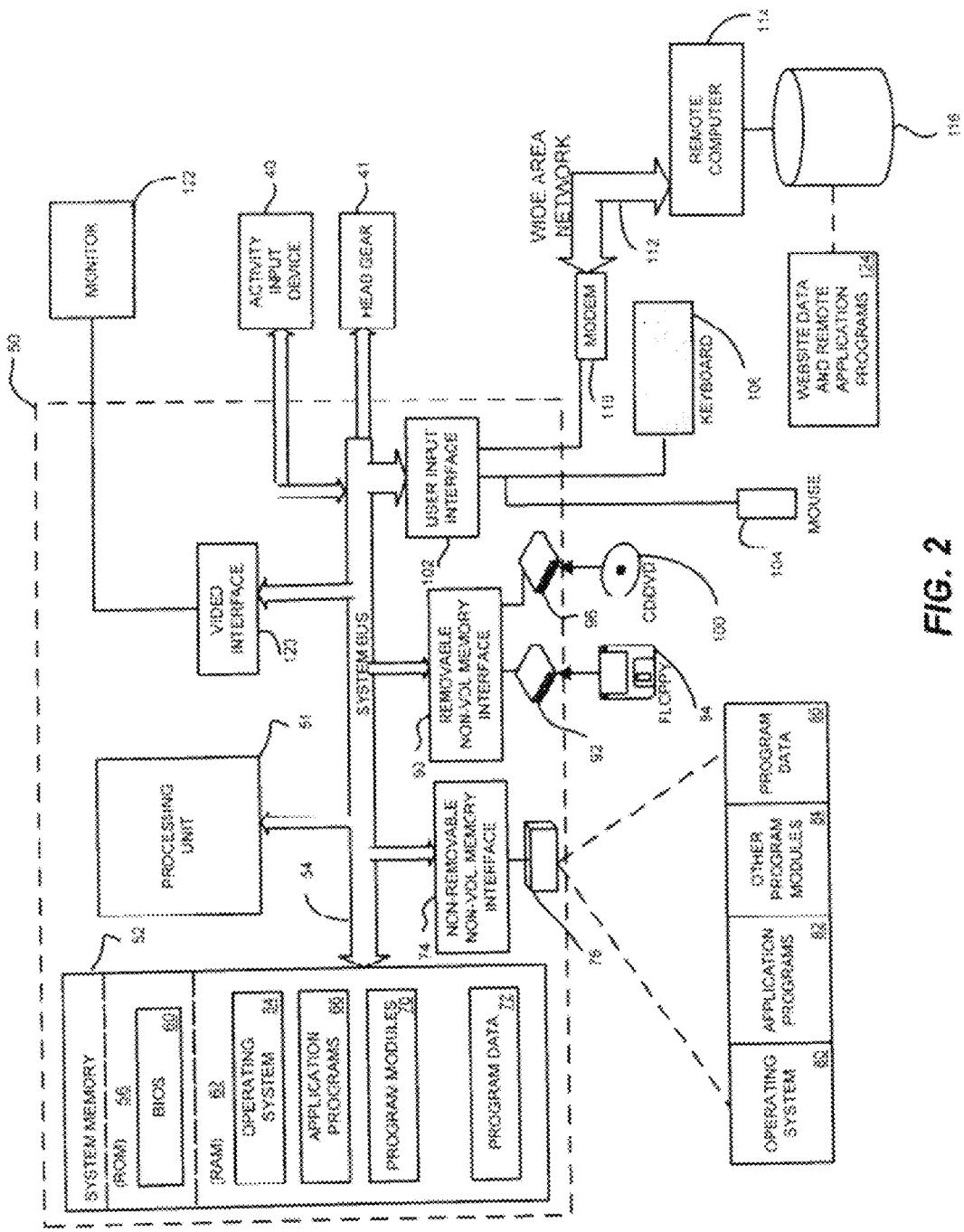
FIG. 2 is a diagram of one example of a general computing device that may operate in accordance with the claims.

FIG. 2 illustrates a typical computing device 50 that may be connected to the network 10 of FIG. 1 and participate in a measuring and computing environment such as the World Wide Web. FIG. 2 may also be an example of an appropriate computing system on which the claimed apparatus and claims may be implemented, however, FIG. 2 is only one example of a suitable computing system and is not intended to limit the scope or function of any claim. Other non-computing systems could also be used as those of ordinary skill in the art will appreciate. The claims are operational with many other general or special purpose computing devices such as PCs 12, server computers 34, portable computing devices such as a laptop 24, consumer electronics 26, wired and wireless activity input devices 40, wired and wireless head gear 41, mainframe computers, or distributed computing environments that include any of the above or similar systems or devices.

With reference to FIG. 2, a system for implementing the steps of the claimed apparatus may include several general computing devices in the form of a computer 50. The computer 50 may include a processing unit, 51, a system memory, 52, and a system bus 54 that couples various system components including the system memory 52 to the processing unit 51. The system bus 54 may include an Industry Standard Architecture (ISA) bus, a Micro Channel Architecture (MCA) bus, Enhanced ISA (EISA) bus, Video Electronics Standards Association (VESA) local bus, a Peripheral Component Interconnect (PCI) bus or a Mezzanine bus, and the Peripheral Component Interconnect Express (PCI-E) bus.

The computer 50 may include an assortment of computer-readable media. Computer-readable media may be any media that may be accessed by the computer 50. By way of example, and not limitation, the media may include both volatile and nonvolatile media, removable and non-removable media. Media may also include computer storage media and communication media. Computer storage media may include volatile and nonvolatile, removable and non-removable media that stores information such as computer-readable instructions, program modules, data structures, or other data. Computer-storage media may include RAM, ROM, EEPROM, or other memory technology, optical storage disks, magnetic storage devices, and any other medium which may be used to store computer-accessible information. Communication media may be computer-readable instructions, data structures, program modules, or other data in a modulated data signal or other transport mechanism. Communication media may include wired media such as a wired network or direct-wired connection, and wireless media such as RF, infrared, and other wireless media.

The system memory 52 may include storage media in the form of volatile and/or non-volatile memory such as ROM 56 and RAM 62. A basic input/output system 60 (BIOS), containing algorithms to transfer information between components within the computer 50, may be stored in ROM 56. Data or program modules that are immediately accessible or are presently in use by the processing unit 51 may be stored in RAM 62. Data normally stored in RAM while the computer 50 is in operation may include an operating system 64, application programs 66, program modules 70, and program data 72.

The computer 50 may also include other storage media such as a hard disk drive 76 that may read from or write to non-removable, non-volatile magnetic media, a magnetic disk drive 251 that reads from or writes to a removable, non-volatile magnetic disk 94, and an optical disk drive 96 that reads from or writes to a removable, nonvolatile optical disk 100. Other storage media that may be used includes magnetic tape cassettes, flash memory cards, digital versatile disks, digital video tape, solid state RAM, and solid state ROM. The hard disk drive 76 may be connected to the system bus 54 through a non-removable memory interface such as interface 74. A magnetic disk drive 92 and optical disk drive 96 may be connected to the system bus 54 by a removable memory interface, such as interface 90.

The disk drives 92, 96 transfer computer-readable instructions, data structures, program modules, and other data for the computer 50 to different storage media 94, 100 for storage. A hard disk drive 76 may store an operating system 64, application programs 66, other program modules 70, and program data 72. These components may be the same or different from operating system 64, application programs 66, other program modules 70 and program data 72. The components associated with the hard disk drive 76 may be different copies than those associated with RAM 62.

The user may interact with the computer 50 through input devices such as a keyboard 106, a pointing device 104 (i.e., a mouse), an activity input device 40, or head gear 41. A user input interface 102 may be coupled to the system bus 54 to allow the input devices to communicate with the processing unit 51. A display device such as a monitor 122 may also be connected to the system bus 54 via a video interface 120.

The computer 50 may operate in a networked environment using logical connections to one or more remote computers 114. The remote computer 114 may be a PC 12, a server 34, a router 20, or other common network node as illustrated in FIG. 1. The remote computer 114 typically includes many or all of the previously-described elements regarding the computer 50, even though only a memory storage device 116 is illustrated in FIG. 2. Logical connections between the computer 50 and one or more remote computers 114 may include a wide area network (WAN) 112. A typical WAN is the Internet. When used in a WAN, the computer 50 may include a modem 110 or other means for establishing communications over the WAN. The modem 110 may be connected to the system bus 54 via the user input interface 102, or other mechanism. In a networked environment, program modules depicted relative to the computer 50, may be stored in the remote memory storage device 116. By way of example, and not limitation, FIG. 2 illustrates website data and remote application programs 124 as residing on the memory device 116. As may be appreciated, other means of establishing a communications link between the computer 50 and the remote computer 114 may be used.

In accordance with the present disclosure, a system and method for altering vision are provided. In particular, the disclosure relates to a system and method of stimulating the retinal ganglion pathways, thereby influencing visual processing and the overall retino-geniculo-cortical pathway. The level and/or type of stimulation may be adjusted according to the visual profile of the individual.

A level of function in retinal ganglion cell types may be assessed to determine a visual processing profile and to identify a need for alteration in one or more subtype of ganglion cells. Generally, three types of major retinal ganglion subtypes are evaluated in the assessment step. Such retinal ganglion cell types may include m-cells, p-cells and k-cells cells. However, fewer or greater types of retinal ganglion subtypes may be evaluated such as, for example, m-cells and non m-cells. The assessment of a functional level in any one of the retinal ganglion cell types is useful in the determination of visual stimulus.

The visual processing profile may be determined using a number of methods known in the art. In certain aspects, the visual profile may include a level of function of the retinal-geniculo-cortical pathway, and in particular, the retinal ganglion cells. Such levels may be based on criteria such as the conduction velocity of the retinal cells. A number of methods known in the art may be used in the determination of retinal ganglion function. For example, steady-state pattern electroretinogram (PERG), optical coherence tomography (OCT), visual function-specific field tests, frequency doubling technology (FDT), Snellen test, contrast sensitivity testing, high-pass resolution perimetry (HRP), short-wavelength automated perimetry (SWAP) and visually evoked potentials (VEP), and multi-focal visually evoked potentials (EVEP) are among the various method useful in assessing visual function associated with the retinal ganglion subtypes. Furthermore, retinal ganglion cell function may be determined by any means developed to stress the specific visual functions associated with each ganglion subtype as described above.

Figure 3A:
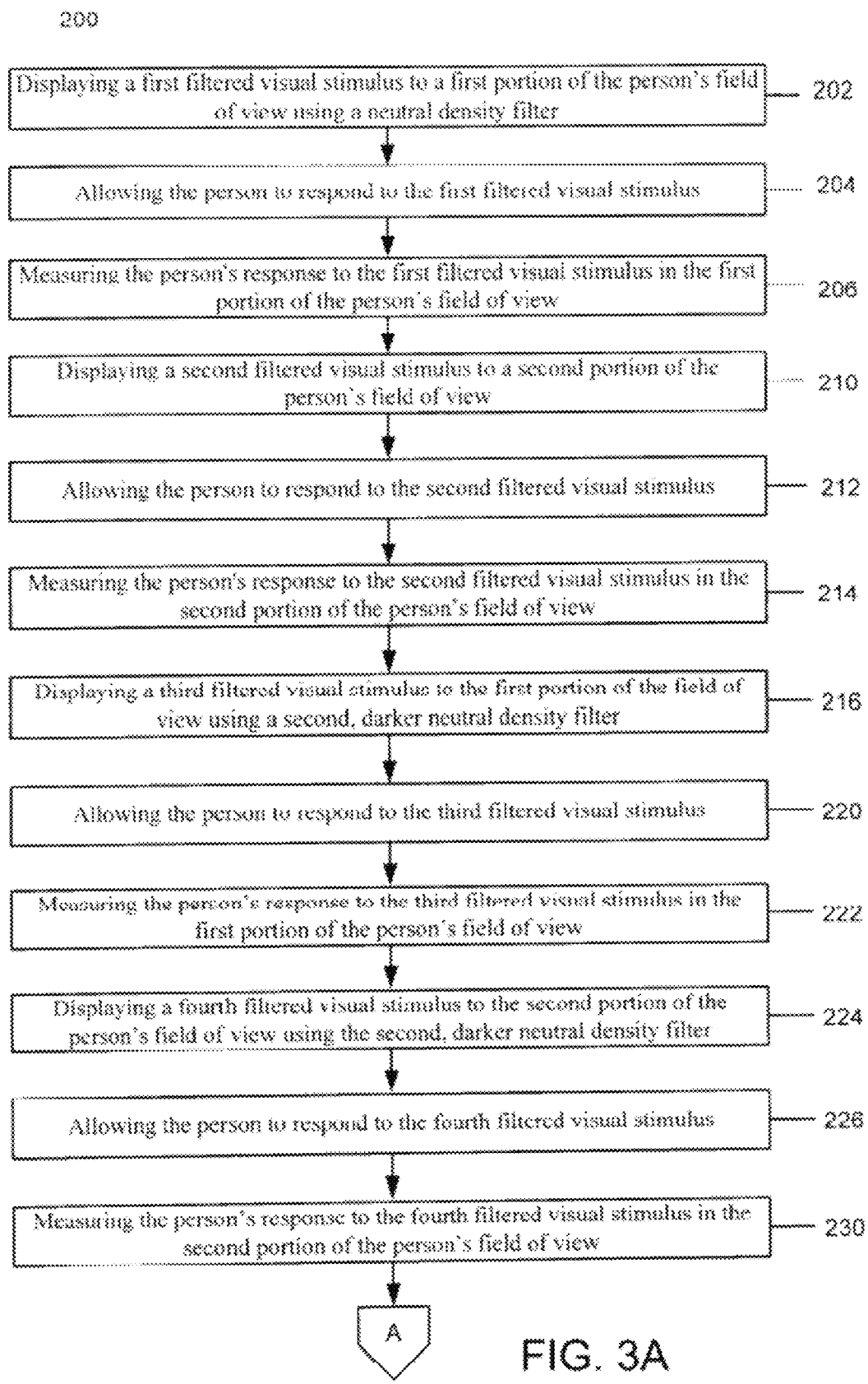
FIGS. 3A and 3B are two parts of a flowchart describing a method of one example of developing a visual processing profile.
Figure 3B:
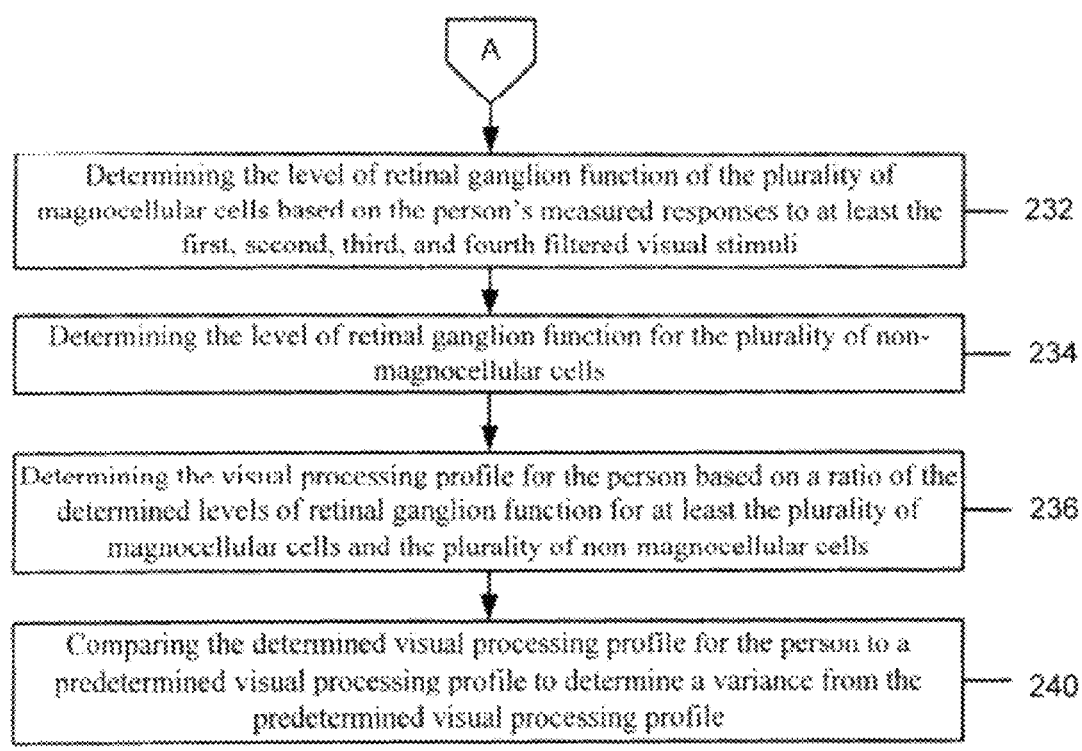

FIGS. 3A and 3B are two parts of an exemplary method 200 of developing a visual processing profile for a person. The method 200 may begin by displaying a first filtered visual stimulus to a first portion of the person's field of view using a neutral density filter (block 202). The visual stimulus could thus be displayed to various portions of the person's field of view, such as, for example, a central portion or a peripheral portion; or within one of those portions, a superior portion, a nasal portion, an inferior portion, a temporal portion, or the entire visual field, etc. The method 200 may then allow the person to respond to the first filtered visual stimulus (block 204). The method may then measure the person's response to the first filtered visual stimulus in the first portion of the person's field of view (block 206).

The method 200 may then display a second filtered visual stimulus to a second portion of the person's field of view (block 210) and allow the person to respond to the second filtered visual stimulus (block 212). The method may then measure the person's response to the second filtered visual stimulus in the peripheral portion of the person's field of view (block 214). The method 200 may then display a third filtered visual stimulus to the first portion of the field of view using a second, darker neutral density filter (block 216) and then allow the person to respond to the third filtered visual stimulus (block 220). The method may also include measuring the person's response to the third filtered visual stimulus in the first portion of the person's field of view (block 222).

After measuring the person's response to the third filtered visual stimulus, the method 200 may display a fourth filtered visual stimulus to the second portion of the person's field of view using the second, darker neutral density filter (block 224) and allow the person to respond to the fourth filtered visual stimulus (block 226). The method 200 may then measure the person's response to the fourth filtered visual stimulus in the second portion of the person's field of view (block 230).

Continuing to FIG. 3B, the method 200 may determine the level of retinal ganglion function of the plurality of magnocellular cells based on at least the person's measured responses to at least the first, second, third, and a fourth filtered visual stimuli (block 232) and determine the level of retinal ganglion function for the plurality of non-magnocellular cells (block 234). This could include the person's p-cells and k-cells, as well as any other subtypes of ganglion cells.

The method 200 may then determined the visual processing profile for the person based on a ratio of the determined levels of retinal ganglion function for at least the plurality of magnocellular cells and the plurality of non-magnocellular cells (blocked 236). The determined visual processing profile for the person may then be compared to a predetermined visual processing profile to determine a variance from a predetermined visual processing profile (block 240).

The predetermined visual processing profile may correspond to a person highly skilled in a particular physical activity based on a ratio of determined levels of retinal ganglion function for at least a first and second retinal ganglion subtypes for the person highly skilled in the particular physical activity. The highly skilled person could be, for example, a professional baseball player, a professional basketball player, a professional football player, a professional tennis player, a professional golfer, a professional race car driver, or other athletes. The predetermined visual processing profile may be calculated by accumulating visual processing profiles for a plurality of people, which could include a plurality of professionals within a professional sport and possibly within professionals having similar positions within the specific professional sport. For example, predetermined visual processing profiles could be created for professional baseball players in separate categories for batting and fielding. This could also be done for other sports where there are substantial differences between offensive and defensive activities.

It should also be noted that the method 200 could alternatively display visual stimuli to other parts of the person's field of view in addition to those described above, or in place of those described above. For example, the method could also display and measure stimuli in a third portion of the person's field of view. It is also possible at the method 200 could incorporate the use of additional neutral density filters to further increase the accuracy of the visual processing profile developed for the person. Alternatively, fewer neutral density filters could be used to determine the person's visual processing profile, or even a completely different technology could be used to measure the levels of retinal ganglion function of the retinal ganglion subtypes when determining the visual processing profile. One example is discussed immediately below.

Figure 4:
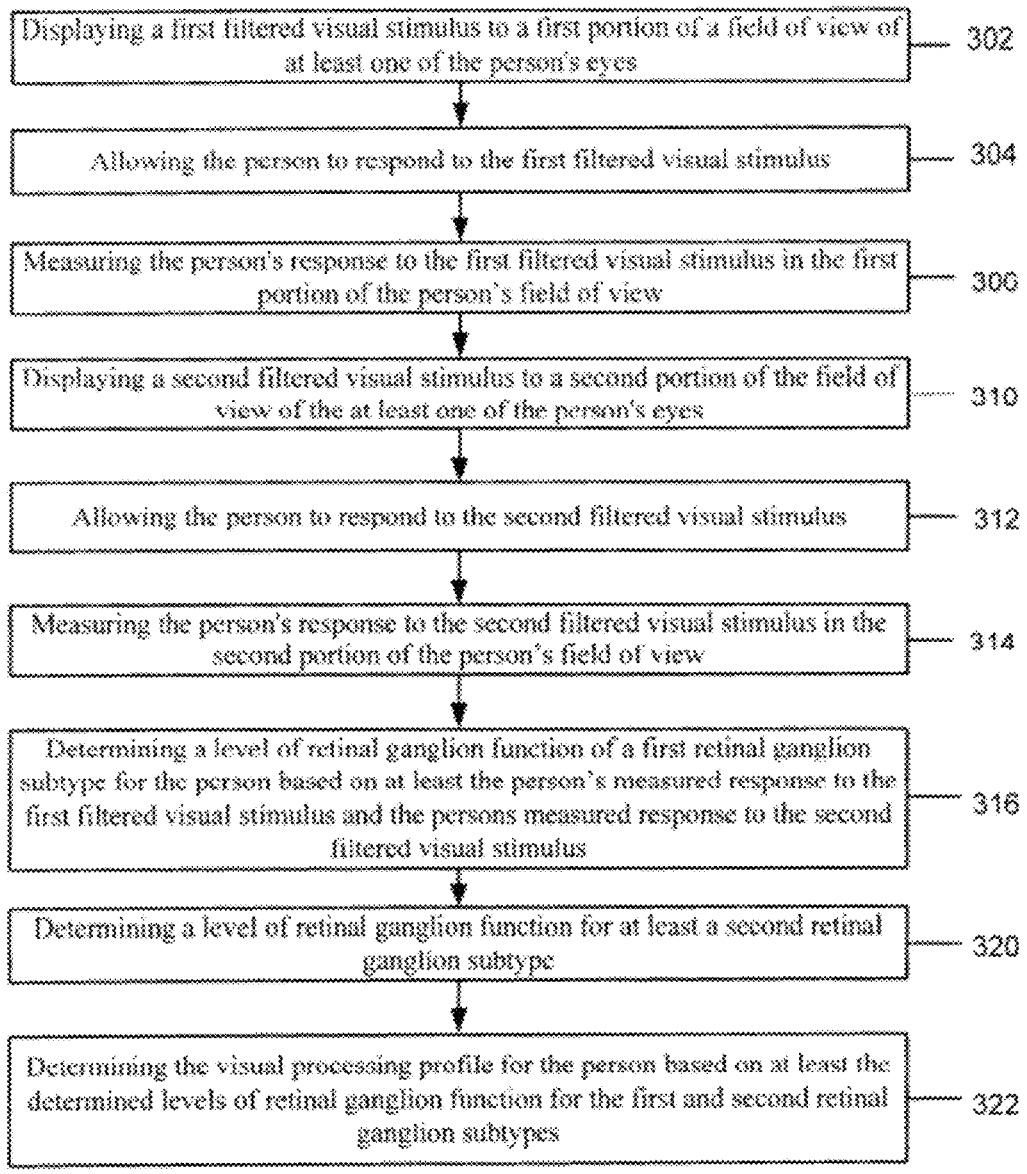
FIG. 4 is a flowchart describing another exemplary method of developing a visual processing profile.

FIG. 4 is an exemplary flowchart of an alternative method 300 of developing a visual processing profile. The method 300 may begin by displaying a first filtered visual stimulus to a first portion of a field of view of at least one of the person's eyes (block 302) and allow the person to respond to the filtered visual stimulus (block 304). The method may then measure a person's response to the first filtered visual stimulus in the first portion of the person's field of view (block 306), display a second filtered visual stimulus to a second portion of the field of view of the at least one of the person's eyes (block 310), and allow the person to respond to the second filtered visual stimulus (block 312).

The method 300 may then measure the person's response to at least the second filtered visual stimulus in at least the second portion of the person's field of view (block 314) and determine a level of retinal ganglion function of at least a first retinal ganglion subtype for the person based on at least the person's measured response to the first filtered visual stimulus and the person's measured response to the second filtered visual stimulus (block 316). The method may then determined a level of retinal ganglion function for at least a second retinal ganglion subtype (block 320) and determine the visual processing profile for the person based on at least the determined levels of retinal ganglion function for at least the first and second retinal ganglion subtypes (block 322).

The determination of a visual profile based on levels of performance may be useful as a diagnostic tool in assessing ability to perform as well as the modification necessary to increase performance. Thus, visual processing profiles could be used, for example, in a career counseling, in assisting patients with health related problems, and identifying people with particular genetic aptitudes (those with eyes having retino-geniculo-cortical pathways capable of providing a competitive advantage), in drafting professional athletes, etc.

In a study performed by testing the visual acuity of athletes with varying performance levels, an association between athletic performance and visual processing associated with particular retinal ganglion cells types was shown. The study focused on baseball players having varying batting averages (BA) and assists. Table 1 shows the results of the study. Visual processing in individuals was measured using the FDT techniques to detect m-cell function. As described in Table 1 below, athletes having an increased batting average showed depression of m-cell function in central middle and peripheral visual fields which is interpreted as an increase in p and k cell function. On the other hand, athletes having lower batting averages showed varying m-cell function in the visual fields. Furthermore, players having higher assists (better fielders) showed increased m-cell function. Neutral density filters were utilized having 0.3 and 0.6 filter densities.

Generally, the visual stimulus is provided to an individual in need of visual modification. The visual stimulus is provided by various means including, but not limited to, computer games, video games, board games, software tools, or other physical objects. In certain embodiments, the visual stimulus is stored and/or displayed in a variety of means known in the art where a user may access the stimulus.

In some embodiments, a visual stimulus is determined to modify function in at least one type of retinal ganglion cell based on the function associated with the cell type. For example, the p-cell and/or k-cell pathways may be stimulated based on association with color sensitivity. As described above, p-cells and k-cells are associated with the red-green and yellow-blue color opponencies, respectively. Thus, a means is provided for determining and/or altering the ratio of p and k-cell function based on stimulation of color opponency pathways.

P-cells mediate red-green color vision via detection of a difference in L and M cone cells. Thus, a red-green system is created to address a low ratio of p-cell function in an individual. In one example, a red stimulus is presented on a green background, or vice versa, and presented to an individual to increase the ratio of p-cell function. Similarly, a blue-yellow system is created to modify the ratio of k-cell function.

TABLE 1

Association Between Batting Statistic and Visual Field Acuity in Baseball Players

| Player | Batting Average | Assist | 0.3 Filter Peripheral Boxes | 0.3 Filter Center Boxes | 0.3 Filter Middle Circle | 0.6 Filter Peripheral Boxes | 0.6 Filter Center Boxes | 0.6 Filter Middle Circle |
|---|---|---|---|---|---|---|---|---|
| 1 | 0.352 | 74 | 18 | 12 | 0 | 35 | 39 | 20 |
| 2 | 0.000 | 0 | 11 | 6 | 10 | 12 | 6 | 10 |
| 3 | 0.316 | 0 | 0 | 0 | 0 | 11 | 0 | 0 |
| 4 | 0.342 | 72 | 8 | 3 | 0 | 16 | 12 | 5 |
| 5 | 0.000 | 0 | 2 | 0 | 5 | 5 | 3 | 0 |
| 6 | 0.288 | 155 | 0 | 0 | 0 | 1 | 0 | 0 |
| 7 | 0.326 | 139 | 13 | 3 | 10 | 25 | 12 | 5 |
| 8 | 0.285 | 125 | 0 | 0 | 0 | 2 | 0 | 0 |

Comparison of the visual profile to the predetermined visual profile provides a level of variance in retinal ganglion subtype cell function. As discussed below, the measured variance may be addressed by creating or generating a visual stimulus to increase or decrease retinal ganglion function, thereby diminishing the variance.

In one instance, a visual profile may be used to address aberrant visual function. The determination of aberrant function may be based on a number of indicia relating to the specific type of visual processing desired by or lacking in an individual. In one example, aberrant function is determined by comparing the level of retinal ganglion function measured to a predetermined level of function.

Once a visual profile is assessed, a visual stimulus is designed to alter processing in at least one retinal ganglion cell type. A means for determining stimulus in response to the level of visual functions associated with at least one cell type may be devised. As will be described in detail below, a visual stimulus may be designed to activate, reduce or terminate function in a particular retinal ganglion cell type based on its associated visual function. Such visual stimulus may be focused to affect conduction velocity, receptive fields, electrical potential rates in other retinal neurons, and action potential rates in retinal ganglion cells. By providing a stimulus that affects the retino-geniculo-cortical pathways in response to the level of function, visual acuity may be altered.

Such systems were tested to determine efficacy in altering visual processing in individuals. Table 2 below shows the differences between retinal ganglion function before and after such stimulus was presented to the individuals. The Tbase mean batting average was determined by assessing visual processing in ten individuals prior to stimulation. Subsequently, those individuals were exposed to stimulation in accordance with the present invention for a time interval of seven minutes. After seven minutes elapsed, the Tseven mean batting average was calculated by assessing visual processing in the ten individuals following stimulation. The statistical significance of the alteration in visual processing following seven minutes of stimulation is shown in Table 3 below, which means that the statistical significance in the improved batting averages was obtained with a P value of less than 0.01 (0.006 actual) confidence level of 99%.

TABLE 2

Paired Samples Statistics

|  | Mean | N | Std. Deviation | Std. Error Mean |
|---|---|---|---|---|
| Tbase | .6300 | 10 | .16700 | .05281 |
| Tseven | .770 | 10 | .15129 | .04784 |

TABLE 3

Association Between Stimulus and Improvement in Visual Processing
Paired Samples Test

| | Paired Differences | | | | | | | |
|---|---|---|---|---|---|---|---|---|
| | | Std. Deviation | Std. Error Mean | 95% Confidence Interval of the Difference | | t | df | Sig. (2-tailed) |
| | Mean | | | Lower | Upper | | | |
| Pair 1 Tbase − Tseven | −.14000 | .12428 | .03930 | −.22890 | −.05110 | −3.562 | 9 | .006 |

Thus, providing a stimulus in accordance with the present disclosure causes a significant alteration in visual processing. In certain aspects, the stimulus color combines with the background color progressively in response to successful visual performance.

M-cells do not show association with chromatic stimulus, thus, an achromatic system of stimulus may be used to determine and modify the ratio of functioning m-cells. The methods and systems of the present disclosure are useful in determination and alteration of retinal ganglion function in adults and children.

Figure 5:
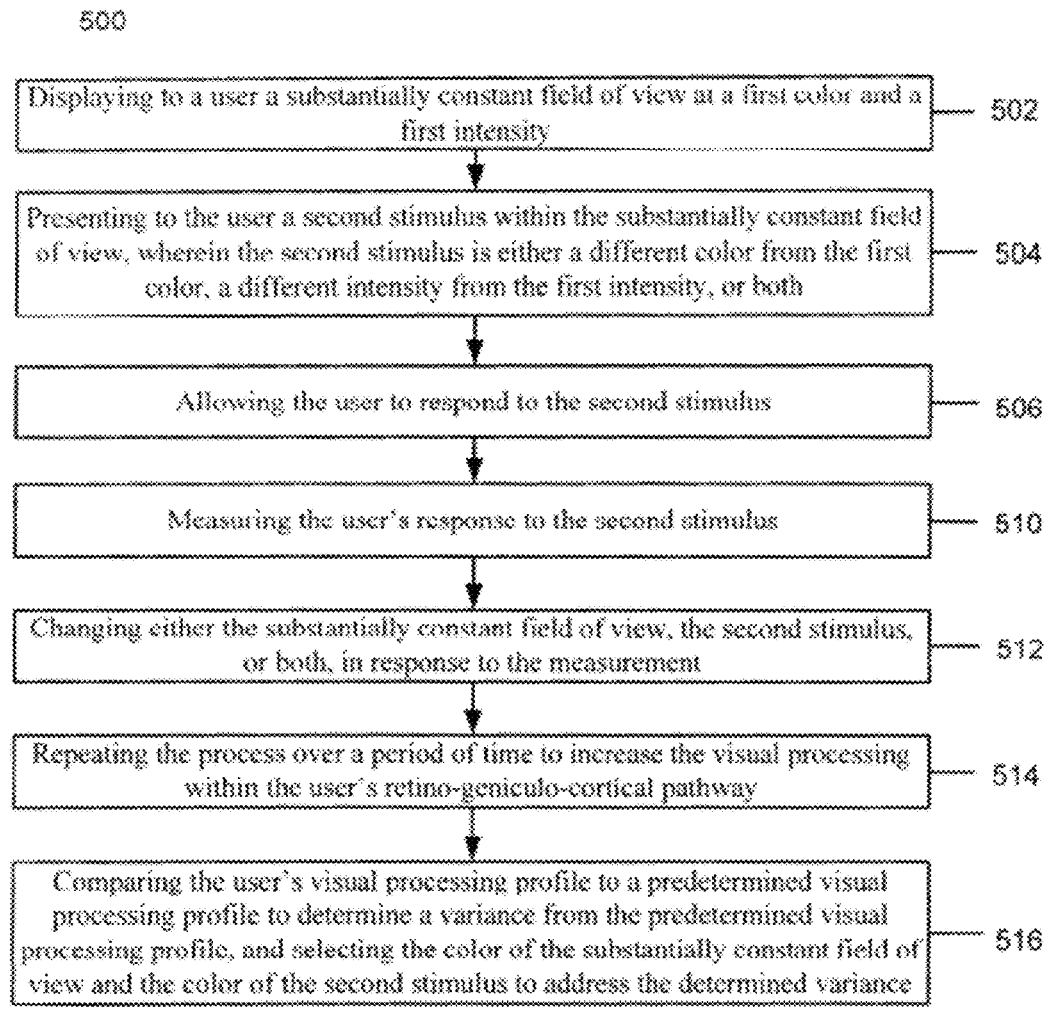
FIG. 5 is a flowchart describing a method of one example of enhancing a retino-geniculo-cortical pathway for a particular activity.

FIG. 5 illustrates an exemplary flowchart 500 of enhancing a retino-geniculo-cortical pathway for a particular activity. The method 500 may begin by displaying to a user a substantially constant field of view at a first color (i.e. wavelength) and a first intensity (block 502) and present to the user a second stimulus within the substantially constant field of view, wherein the second stimulus is either a different color from the first color, a different intensity from the first intensity, or both (block 504). The second stimulus may model a movement of an object toward or away from a user. The method may also include allowing the user to respond to the second stimulus (block 506), measuring the user's response to the second stimulus (block 510), and changing either the substantially constant field of view, the second stimulus, or both, in response to the measurement (block 512). The method may change the second stimulus by either decreasing or increasing the intensity of the second stimulus, or by changing the color of the second stimulus, or both. It is possible that the change to either the constant field of view, the second stimulus, or both, may be performed in real time in response to the measurements.

The method 500 may then repeat the process over a period of time to increase the visual processing within the user's retino-geniculo-cortical pathway (block 514). This process may be repeated for about five to ten minutes, or for approximately seven minutes. However, alternative lengths of time may be used within a particular system. The method may then compare the user's visual processing profile to a predetermined visual processing profile to determine a variance from the predetermined visual processing profile, and select the color of the substantially constant field of view and the color of the second stimulus to address the determined variance (block 516).

The color of the substantially constant field of view and the color of the second stimulus may be selected based on a visual processing profile previously determined for the user. In other words, the color of the substantially constant field of view and the color of the second stimulus may be selected based on a ratio of levels of retinal ganglion function for a plurality of magnocellular cells and a plurality of non-magnocellular cells. Thus, increasing the visual processing within the user's retino-geniculo-cortical pathway involves increasing the user's visual processing in at least one sub-type of the user's retinal ganglion cells.

While not shown in FIG. 5, the method of 500 may include varying the degree of changes based on the measured responses. For example, the intensity of the second stimulus may be decreased at a greater rate if the user's measured responses are exceedingly accurate. Likewise, the intensity of the second stimulus may be decreased at a slower rate, or even increased, if the user's measured responses become worse (i.e., the user fails to see the second stimulus or fails to see the second stimulus in time to generate an appropriate response).

The method of 500 may also adjust the presentation to the user of the second stimulus by adjusting the position of the second stimulus within the substantially constant field of view. This adjustment may be performed automatically based on a specific enhancement identified by the user. For example, the user could indicate that he wishes to work on and enhance a specific area of ganglion cells by repeatedly responding to retino-geniculo-cortical pathway stimulation in a specific quadrant of the user's field of view.

After repeating the process over a period of time, the user may then perform the actual physical activity within a set period time, and will likely see a marked improvement in his or her performance.

Figure 6:
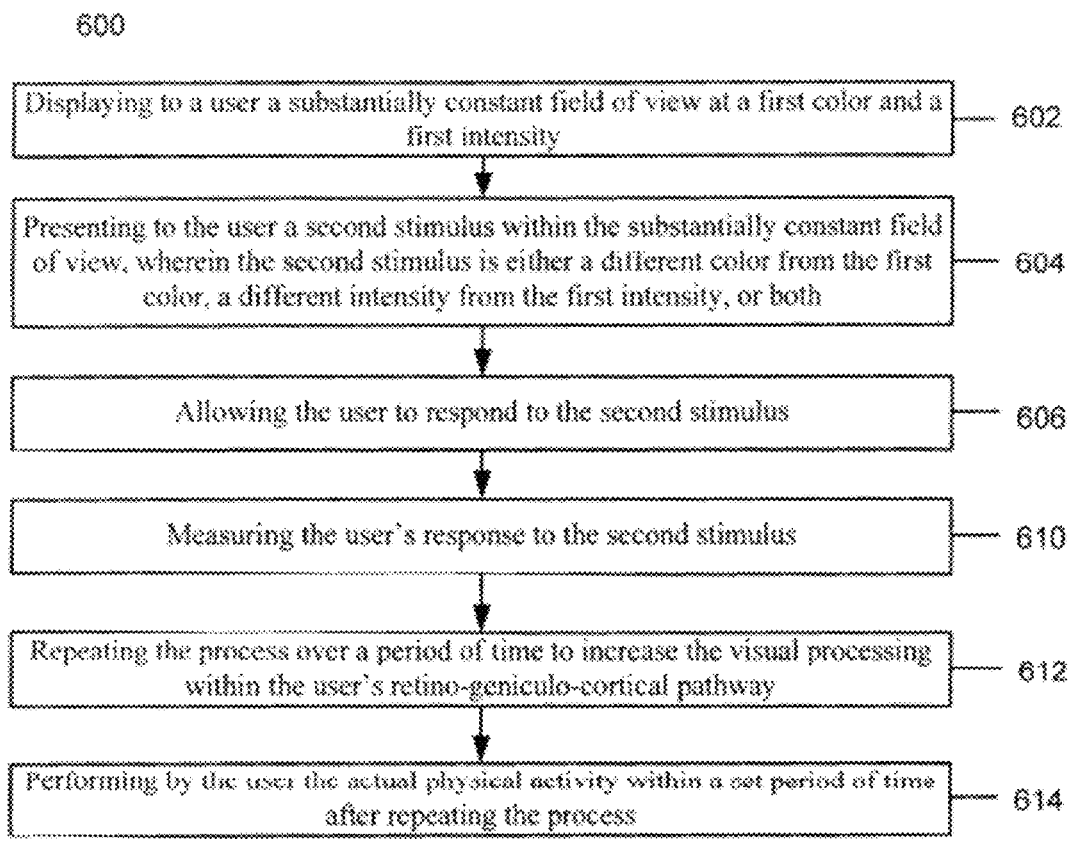
FIG. 6 is a flowchart describing another exemplary method of enhancing a retino-geniculo-cortical pathway for a particular activity.

FIG. 6 illustrates an exemplary alternative flowchart 600 of enhancing a retino-geniculo-cortical pathway for a particular activity. The method 600 may begin by displaying to a user a substantially constant field of view at a first color (i.e. wavelength) and a first intensity (block 602) and present to the user a second stimulus within the substantially constant field of view, wherein the second stimulus is either a different color from the first color, a different intensity from the first intensity, a modified frequency of display (i.e., flicker or motion), or a combination (block 604). The method may also include allowing the user to respond to the second stimulus (block 606) and measuring the user's response to the second stimulus (block 610).

The method 600 may then repeat the process over a period of time to increase the visual processing within the user's retino-geniculo-cortical pathway (block 614). Thereafter, the user may then perform the actual physical activity within a set period time.

Figure 7:
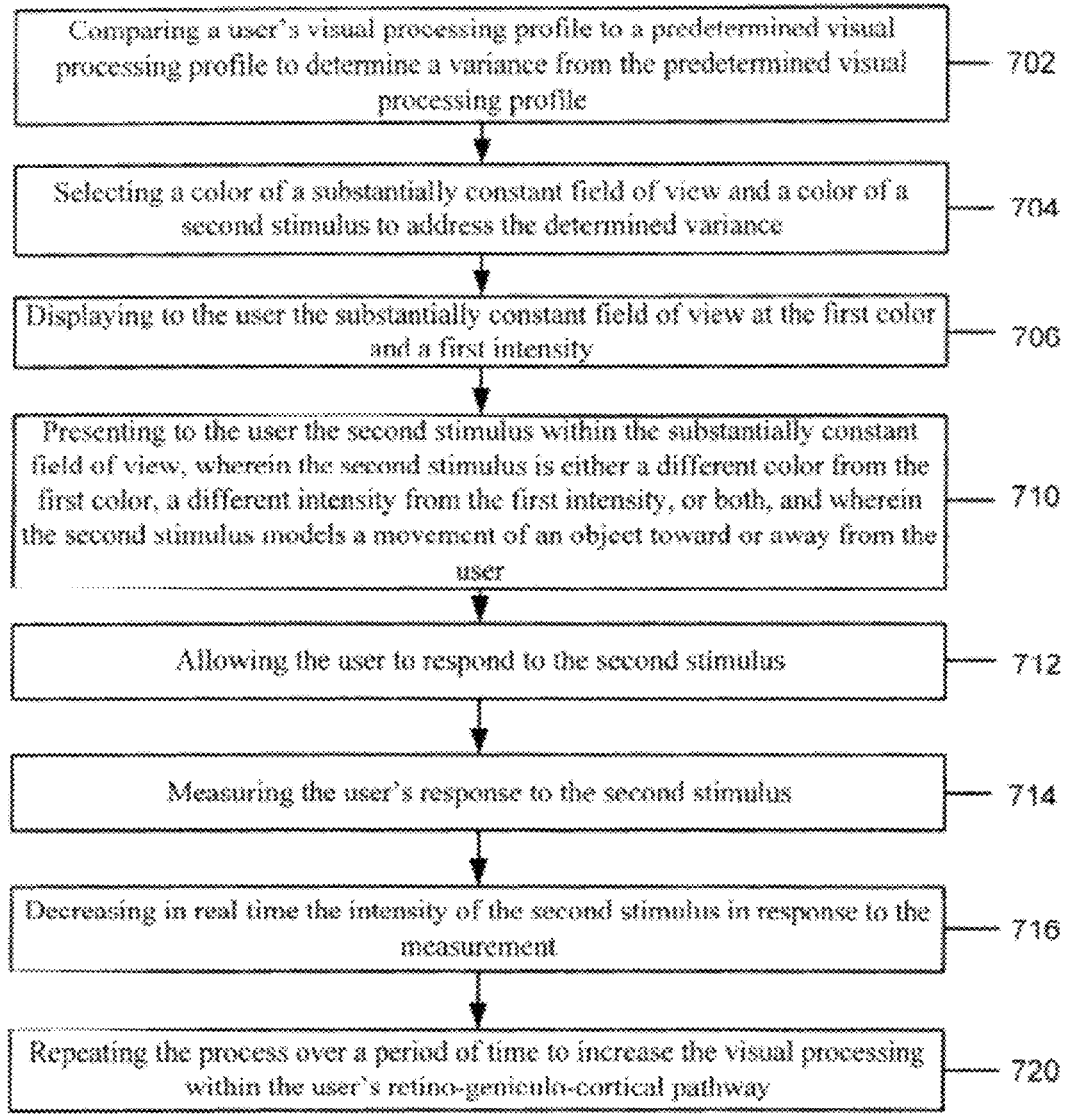
FIG. 7 is a flowchart describing another exemplary method of enhancing a retino-geniculo-cortical pathway for a particular activity.

FIG. 7 illustrates a flowchart 700 illustrating another exemplary method of enhancing a retino-geniculo-cortical pathway for a particular activity. The method 700 may begin by comparing a user's visual processing profile to a predetermined visual processing profile to determine a variance from the predetermined visual processing profile (block 702) and selecting a color of a substantially constant field of view and a color of a second stimulus to address the determined variance (block 704). The method may then display to the user to substantially constant field of view at the first color and a first intensity (block 706) and present to the user the second stimulus within the substantially constant field of view, wherein the second stimulus is either a different color from the first color, a different intensity from the first intensity, or both, and wherein the second stimulus models a movement of an object toward or away from the user (block 710).

The method 700 may then allow the user to respond to the second stimulus (block 712), measure the user's response to the second stimulus (block 714), decrease in real-time the intensity of the second stimulus and response to the measurement (block 716), and repeat the process over a period of time to increase the visual processing within the user's retino-geniculo-cortical pathway (block 720).

The disclosure is based on determination and alteration of visual profiles based on levels of retinal ganglion cell function. The disclosed methods are designed to stimulate visual pathways associated with one or more specific retinal ganglion cell types, thereby altering the ratio of function in these retinal ganglion cell types. Thus, the disclosed methods may be used to diagnose, develop and alter visual profiles based on the function of at least one type of retinal ganglion cell.

Baseball Gaming Environment

Figure 8:
FIG. 8 illustrates an overview display of a baseball gaming embodiment.

FIG. 8 illustrates an overview screen of a gaming embodiment for improving a player's visual processing profile using a game of baseball. The gaming embodiment may be implemented on a computing system such as the one described in FIGS. 1-3. The principles described above may be implemented using the illustrated gaming embodiment to improve a player's skill in hitting a baseball. It should be noted that while a baseball game embodiment is described in detail below, the process described may be applicable to other fielding activities such as, for example, football, hockey, tennis, golf, soccer, etc.

Figure 9:
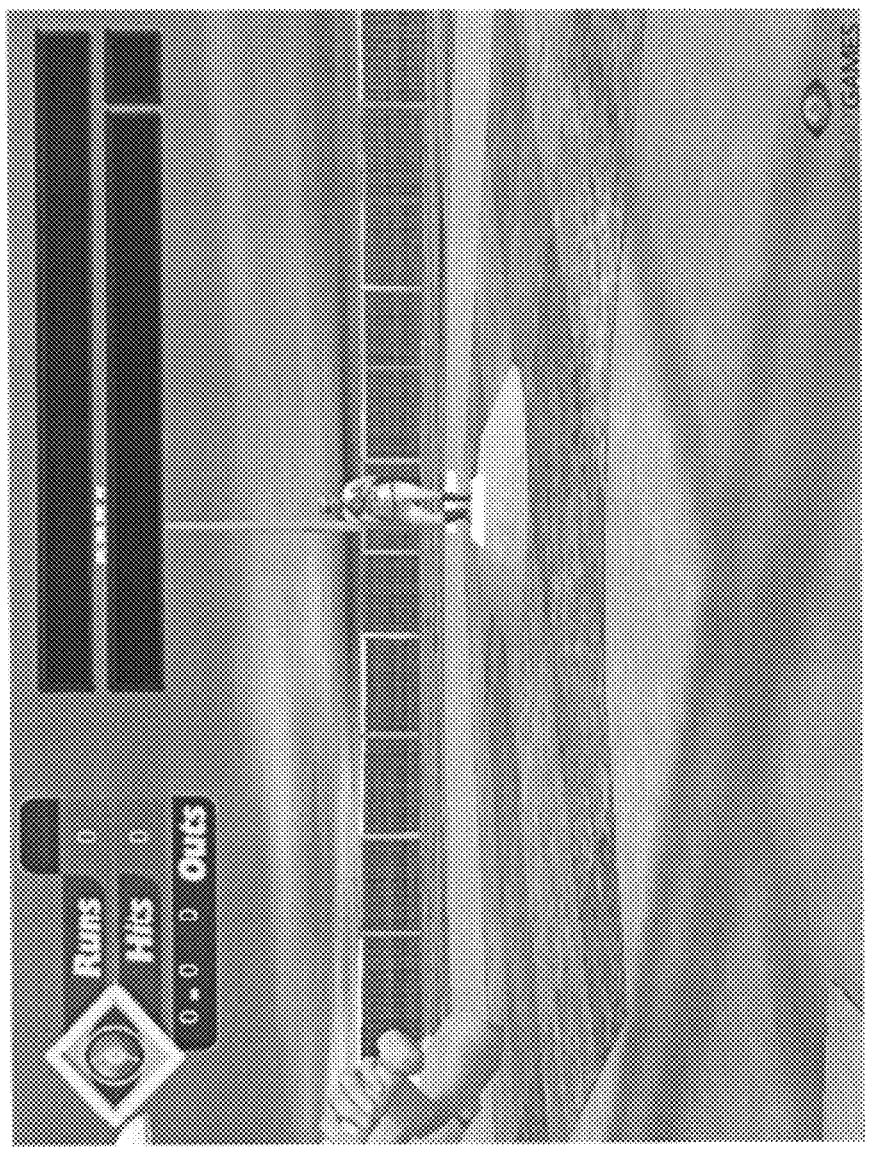
FIG. 9 illustrates a screen display from a perspective of a batter/player.
Figure 10:
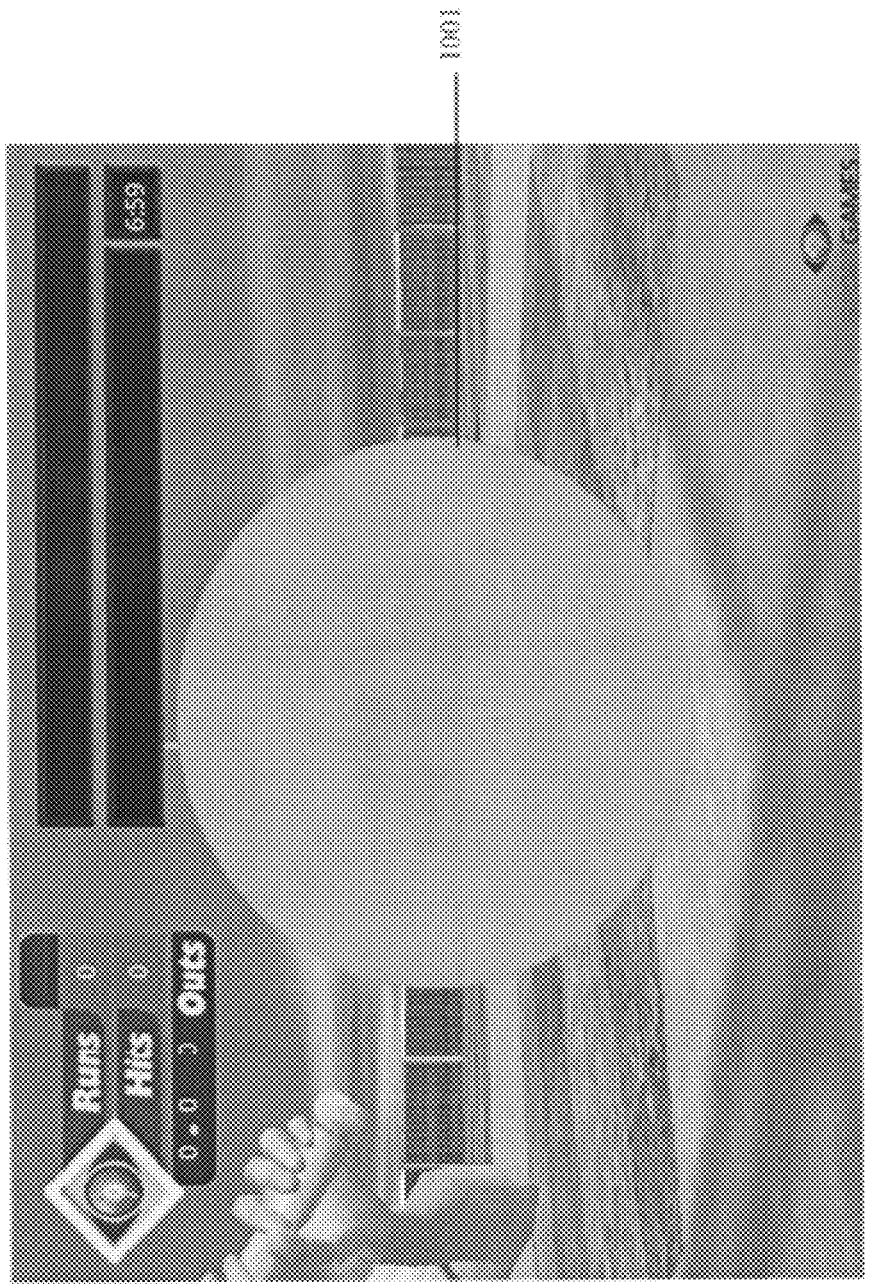
FIG. 10 illustrates a display of a batter's view with a first field of view of constant intensity and color.

Generally, FIG. 8 illustrates a top view of a baseball field 800 where a pitcher 802 is shown on a pitcher's mound 804, and a batter 806 is situated at a home plate 808. During game play, a screen shot from a perspective of the batter 806 may be shown, as illustrated in FIG. 9. In this game, a player in the game embodiment may step into the role of a batter 806. While a clear view to the pitcher is illustrated in FIG. 9, during game play a substantially constant first field of view 1001 at a first color and a first intensity may be displayed in at least a portion of the batter's view, as illustrated in FIG. 10. In at least one embodiment, the first color of the first field of view 1001 may be green. In at least one embodiment, the first field of view 1001 may be positioned such that it covers a batter's view of a strike zone. The size of the first field of view may be set or adjusted based on an estimated distance that the player's eyes are from the display. As illustrated in FIG. 10, a view of the pitcher may be partially obscured depending on the intensity (e.g., luminance) or color of the first field 1001.

Figure 11:
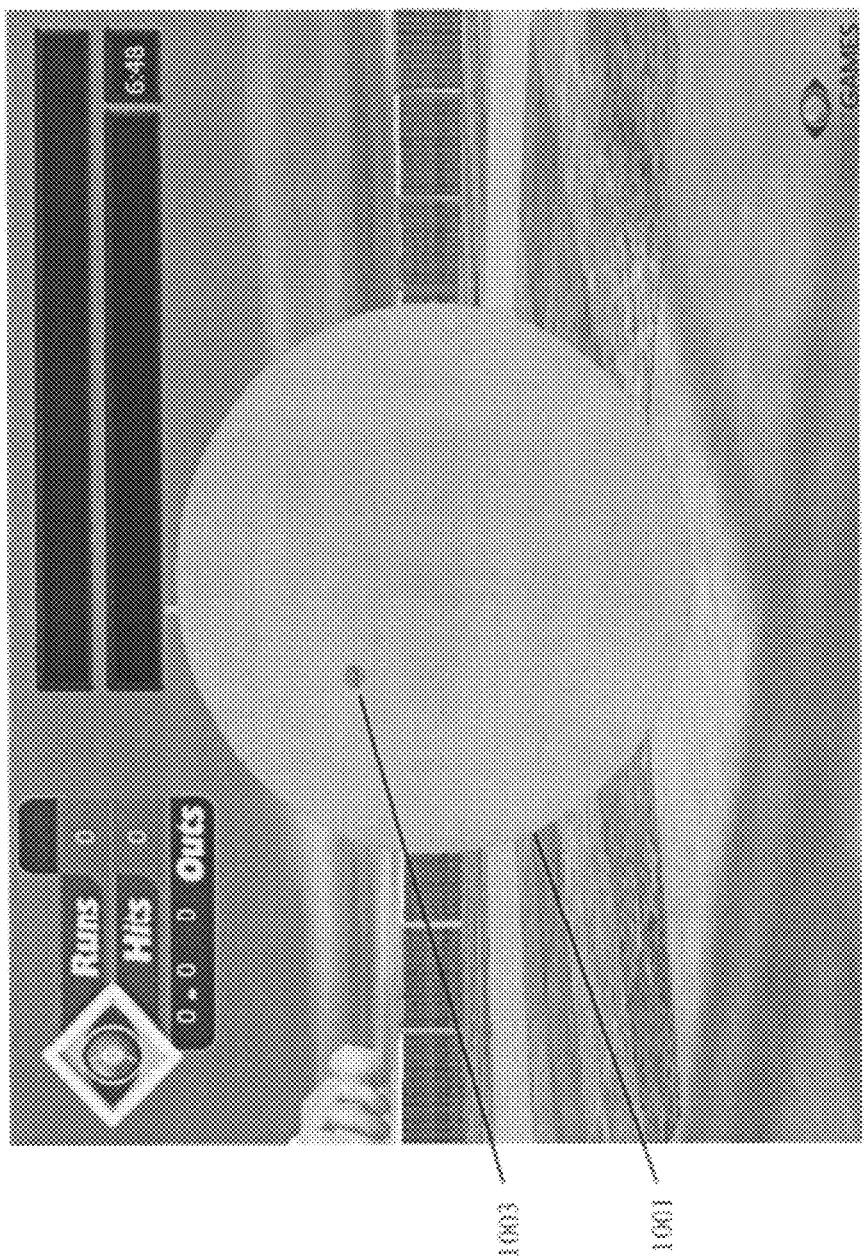
FIG. 11 illustrates a screen shot of a ball pitched towards the batter or player within a first field of view.

In operation, the game embodiment may display the pitcher 802 launching or throwing a pitch towards home plate 808, where the path of the pitched ball is at least partly within the substantially constant first field of view 1001. FIG. 11 illustrates a screen shot of a ball 1003 pitched towards the batter or player. In this manner, the ball 1003 may represent a second stimulus within the substantially constant first field of view 1001, where the ball 1003 is either a different color from the first field of view 1001 (e.g., white with black inseams) and/or a different intensity from the first field of view 1001.

In at least one embodiment, the distance, time, and path traveled by the pitched ball may correspond to a typical pitch between home plate and a pitcher's mound in a particular league of baseball. For example, in at least one embodiment, the game may simulate the actual time for the ball to travel 60.5 feet at various pitch speeds and use real world observed reactions times to compute a reaction window for the player. This real world behavior may be incorporated into the game to correspond to the time the batter has to see the pitch, to register the pitch, and then to formulate a physical reaction. The real reaction time could also be encompassed into other sports, such as, for example, a quarterback's three step drop.

Figure 12:
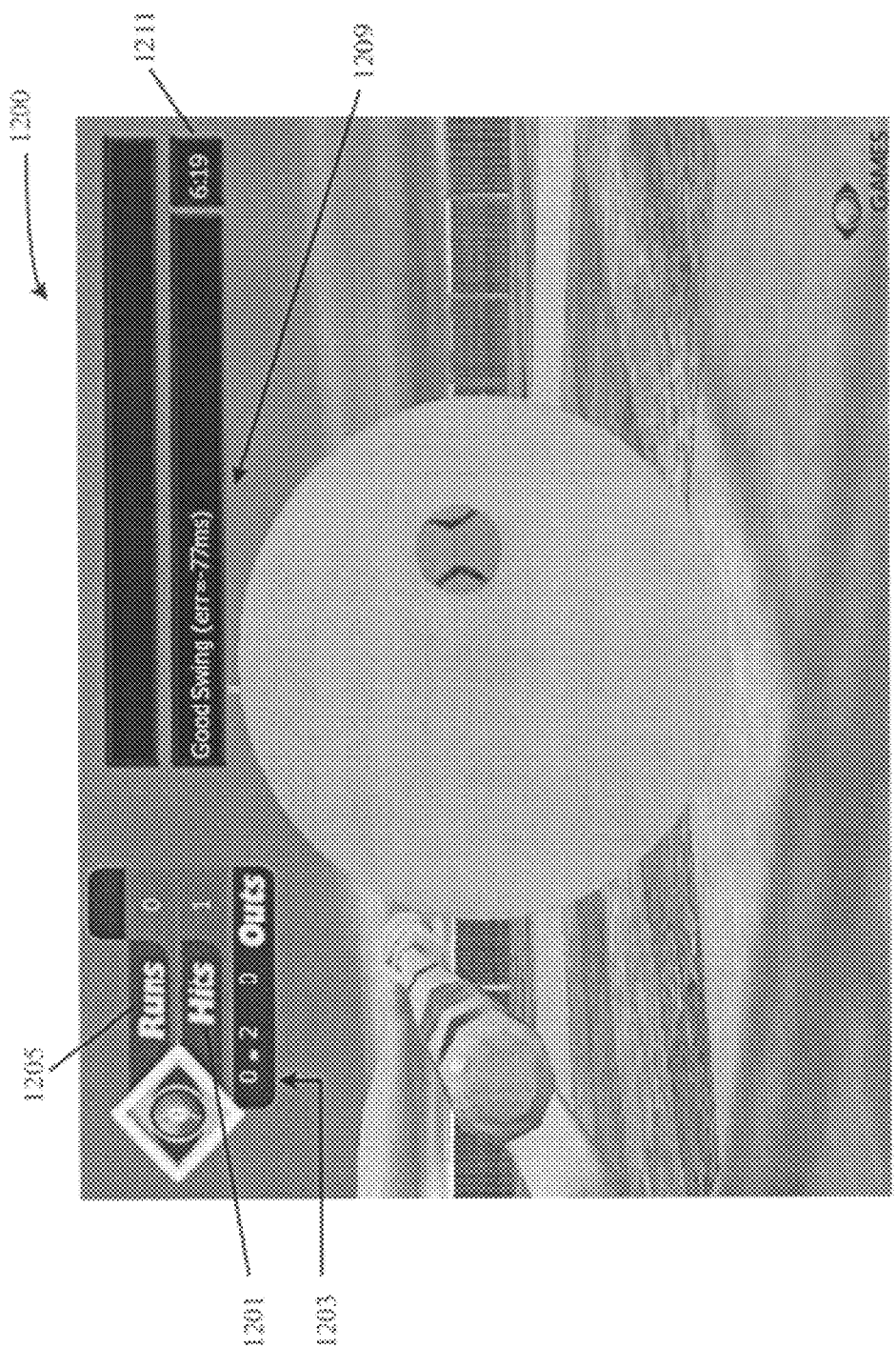
FIG. 12 illustrates display of a baseball traveling through a batter's strike zone with the batter initiating a swing of the bat.

In at least one embodiment, the game may allow a player to react to the second stimulus using a user interface, such as a computer keyboard or mouse. In operation, the game embodiment may allow the player, acting as batter, to provide an input (e.g., using a computer keyboard) to initiate a swing of the batter's bat. For example, the player may press a key (e.g., a space bar) to initiate the swing of the bat. In one embodiment, the rate, velocity, angle and/or path of the batter's swing may remain constant for each press of the key. FIG. 11 illustrates a pitch being initiated by a pitcher, while FIG. 12 illustrates the baseball traveling through a batter's strike zone with the batter initiating a swing of the bat. If the player initiates the swing at a predetermined time, the game embodiment may show contact of the bat with the pitched ball and indicate a hit. Otherwise, the game may indicate a miss. As discussed above, the computer gaming embodiment may be programmed to use real world observed reactions times to compute a predetermined reaction window for the player, where the reaction window corresponds to times in which the initiation of the swing by the player may result in a hit. When the player initiates a swing outside the predetermined reaction window, the game may indicate a miss.

A player's reaction to the pitch may be measured and recorded. According to an embodiment, the process of pitching a ball, allowing the user to react to the pitch, and recording the user's reaction may be repeated several times. In one embodiment, parameters of the game may be displayed on the screen 1200. The parameters may include the number of hits 1201 and the number of strikes or misses 1203 during the current game play. Runs 1205 may be randomly assigned or based on the type of pitch and the player's reaction. In the display of FIG. 12, the timeliness of the pitch may be displayed 1209. For example, if the player initiated a swing too early, an early swing may be indicated including how early the swing was initiated from the correct time. Similarly, if the swing was late, the display may indicate that the swing was initiated late and how late the swing was initiated. The display may also indicate a duration of game play 1211. As discussed further below, the duration and other statistics may be parameters that are settable by the player.

According to an embodiment, during the repeated process of pitching balls to the player and recording player reaction, the substantially constant first field of view 1001 may be changed (e.g., the first color or first intensity may be changed). In addition, the display of the pitch may be changed, which corresponds to a change in the second stimulus. For example, the intensity of the display of the ball may be changed, or the color of the ball may be changed, or both. In at least one embodiment further described below, changes to the display of the first field or of the pitched ball may be performed in response to measured player reactions to the pitches.

Luminance Algorithm

Figure 13:
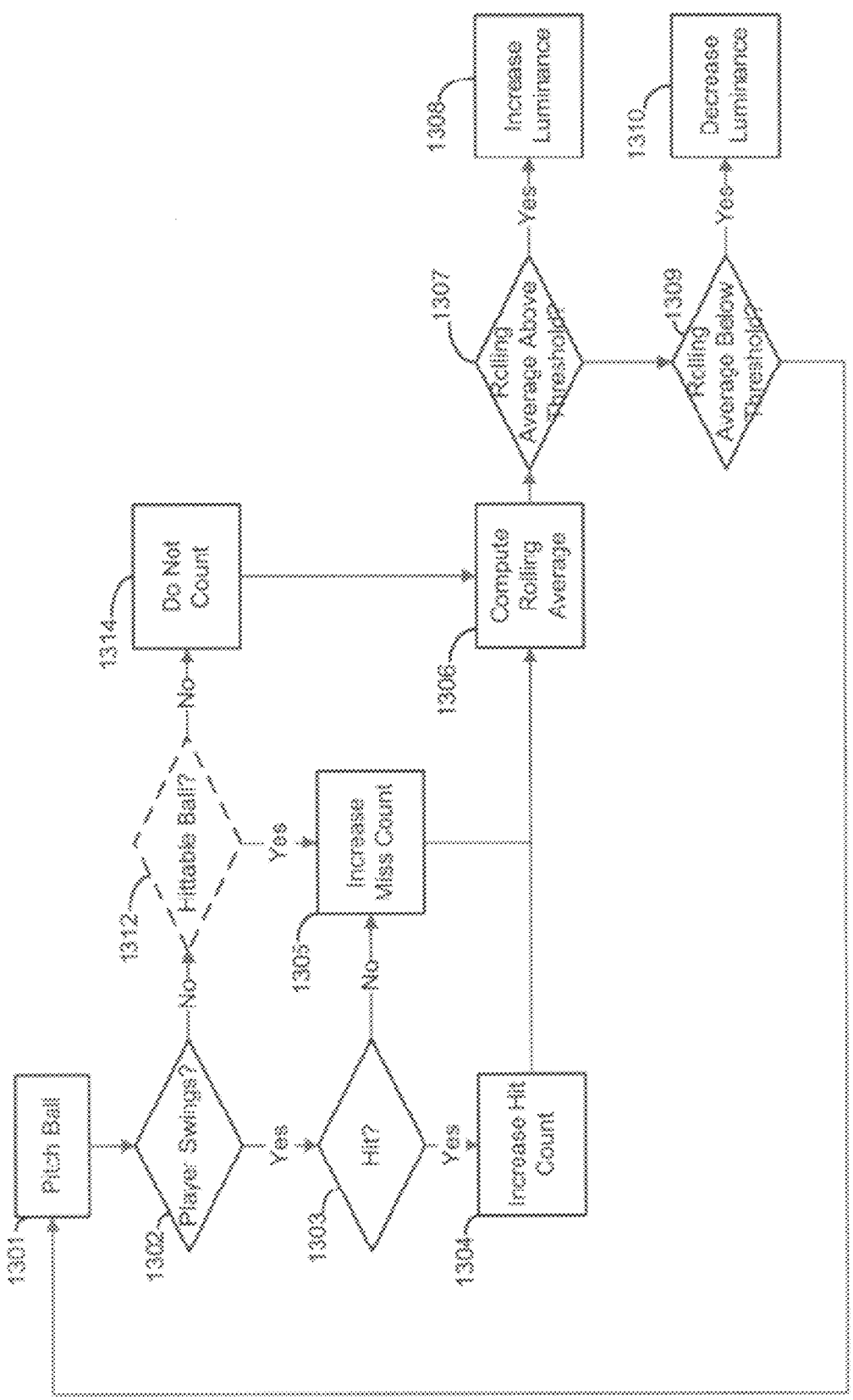
FIG. 13 illustrates a process of adjusting luminance of a pitched ball.

In one embodiment, the luminance of the pitched ball may be modified based on a luminance algorithm that tracks a running history of hits and misses of the pitched ball during operation of the game. In this embodiment, a hit or miss by the player may be recorded in a history buffer (e.g., a data storage medium). The game may be programmed to compute a rolling average of a parameter of the game based on player reactions. For example, a rolling average may be computed based on the hits to misses ratio or hits to total pitches ratio. FIG. 13 illustrates a process flow for adjusting the luminance based on a rolling batting average (hits to misses). In block 1301, a ball may be pitched and the reaction of the player recorded. Block 1302 may determine whether the player initiated a swing. If the player swung at the ball, block 1303 may determine whether the player hit or missed the ball. As discussed above, this may depend on whether the player initiated a swing during a predetermined reaction window for the pitch. If swing was a hit, then a hit counter may be incremented 1304. If the swing was a miss, then a miss counter may be incremented 1305. Next, the game may be programmed to periodically track or calculate the rolling average 1306. If the rolling average increases or decreases pass a threshold, luminance of the ball may be adjusted. For example, if the rolling average increases past a threshold 1307, the luminance may be increased 1308. Similarly, if the rolling average of hits to misses decreases past a threshold 1309, the luminance may be decreased 1310. Threshold values may be selected to provide a visually subtle change in the luminance.

It should be noted that one effect of changing the luminance is that the ball may become more difficult or easier to see by the player. This change in luminance may alter or modify the player's visual processing profile. As discussed above, the process of pitching the ball to the player against the first field and recording the player's reaction may be repeated several times. In at least one embodiment, a computing may be configured to launch one pitch after another until a particular duration of time or game play has expired. In at least one embodiment, the pitching may be repeated for about five to ten minutes, or for approximately seven minutes. However, alternative lengths of time may be used within a particular system. It should be noted that in some field tests, a duration of seven minutes was found to be sufficient to alter the user's visual processing profile. Thus, in at least one embodiment, the duration of game play may be limited to about seven minutes.

FIG. 13 further illustrates that if the player does not swing at the ball 1302, then it may be further determined at block 1312, whether the pitch was a hittable pitch. If the ball was not hittable 1314, then the pitch may be removed from the count of the batting average. In this manner, a player may not be penalized for foregoing a swing at a non-hittable ball. If the ball was hittable and the player did not swing, then the pitch may count as a miss 1305. Whether or not the ball is hittable may depend on further parameters discussed below.

In another embodiment, the program may adapt the game to a given user's visual abilities by further tracking various aspects of the user's input history. In one embodiment, the program may take into account three or more consecutive failures of the user to swing at the pitches, particular hittable pitches, in determining the luminance or other visual characteristic. In other embodiments, the program may take into account consecutive early swings, consecutive late swings, and so forth, as part of the luminance determination.

Figure 14:
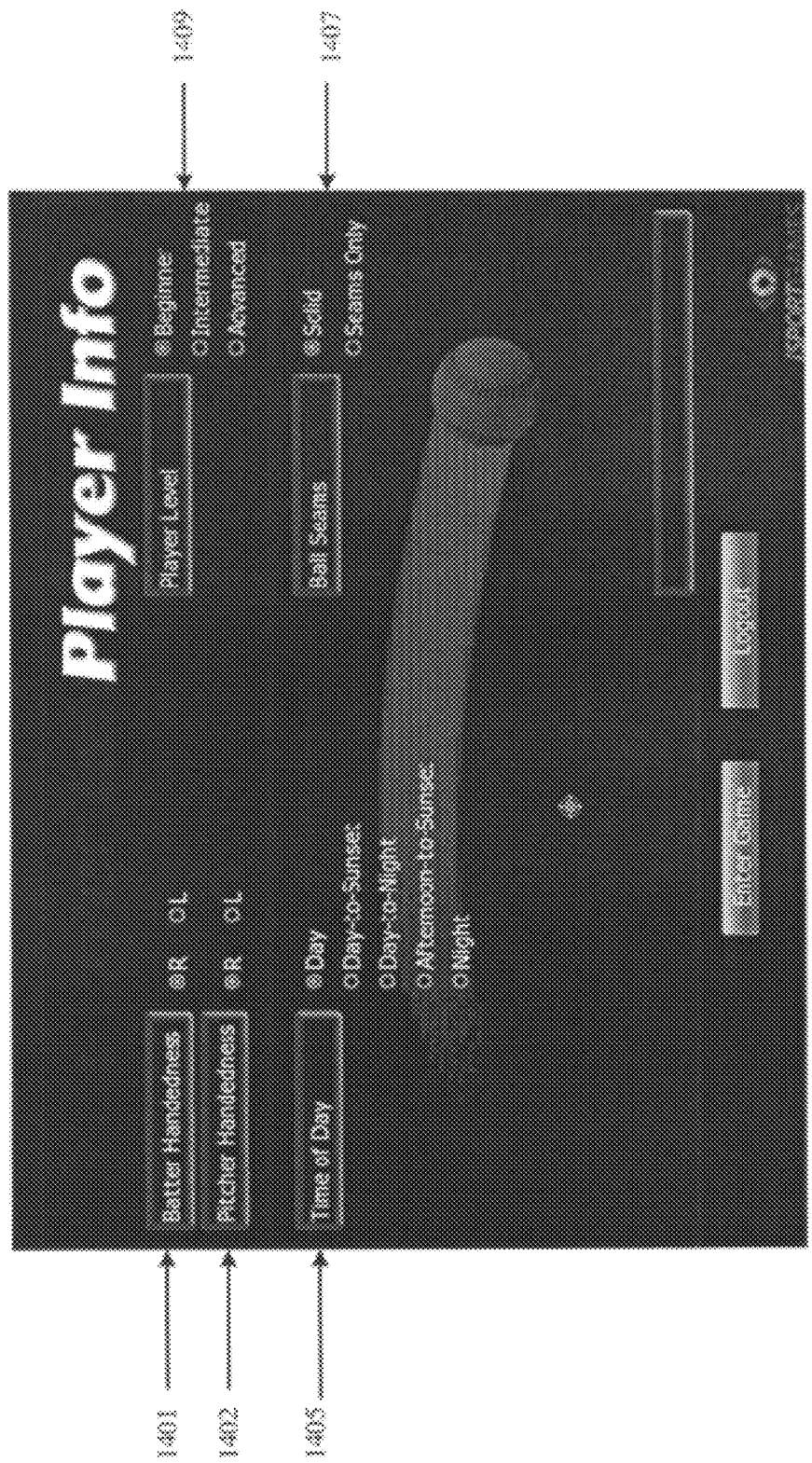
FIG. 14 illustrates parameters that may be used to adjust the display of a pitched ball.

FIG. 14 illustrates further parameters that may be used to adjust the display of the pitched ball based on user reaction. In this embodiment, a batter handedness parameter 1401 may be used to designate whether the batter is right handed or left handed. A selection of a right handed batter may position the displayed player on the left side of home plate (from the view of the batter) and a selection of a left handed batter may position the displayed player on the right side of home plate. Another game parameter may be the handedness of the pitcher 1402. Right handed and left handed pitcher selection may determine how the pitch is launched from the pitcher to the batter.

Another parameter that may be set by the player is the time of day 1405. A day value or a night value may correspond to a constant field illumination and reflectance of light off the pitched ball. Night settings may simulate artificial field lights (e.g., lamps) while day settings may simulate daylight.

Time of day settings showing a transition may include day-to-sunset, day-to-night, and afternoon-to-sunset. These settings may provide a field illumination, glare, and reflection of light off the ball that changes during the duration of game play. Accordingly, shadows on the field may shift and move as well with one of the transition lighting settings.

A ball seams parameter 1407 may be set to display the pitched ball as a solid spherical shape (solid) or a translucent shape having solidly displayed ball seams. This setting may be used to assist a player in tracking the movement of a ball based on highlighting the body of the ball or the ball seams.

FIG. 14 further illustrates that player level may be a selectable parameter 1409. According to one embodiment, the player level setting may invoke an algorithm that affects the display of the ball based on which level is selected. In one embodiment, an aspect of the ball display that may be changed is luminance of the pitched ball.

When the player level is selected to be a beginner level, all balls pitched to the batter may be hittable. A beginner level may simply apply the luminance algorithm as described in FIG. 13 to all pitches, where block 1312 may not be realized since all balls pitched to the batter may be hittable. A hittable ball may mean that the ball will be pitched to land within the strike zone of the player.

Figure 15:
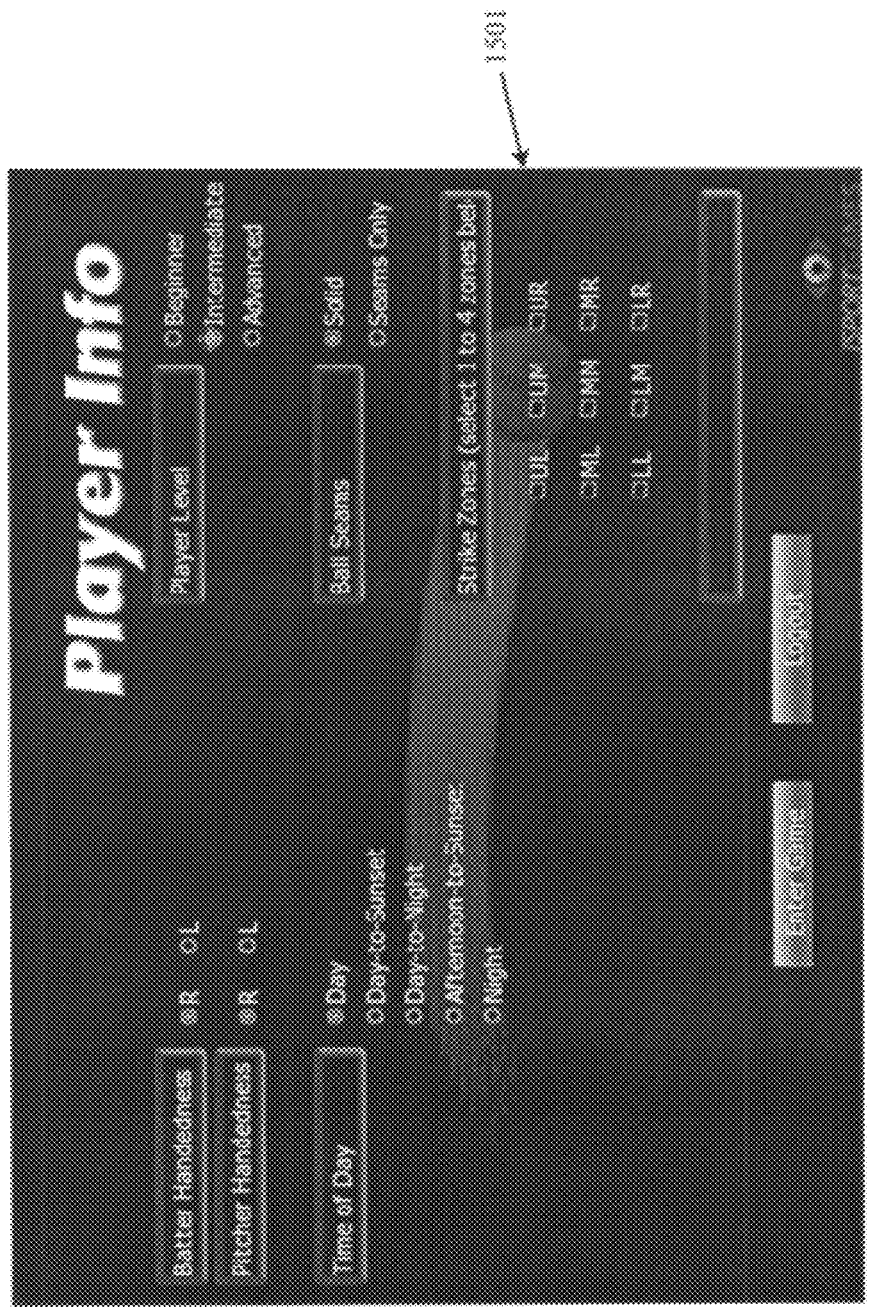
FIG. 15 illustrates a configuration screen for an intermediate player level.

When the player level is selected to be intermediate, not every ball may be pitched in a designated strike zone area of the batter. As illustrated in FIG. 15, when the intermediate player level is selected, additional options for strike zone areas 1501 may be displayed to the player. At the intermediate level, the player may be allowed to select one or more of the strike zones (e.g., up to 4 strike zones may be selected in the embodiment of FIG. 14). The selection of a strike zone area may indicate that the user is interested in developing his swing or reaction to balls pitched to the selected strike zone area. In one embodiment, the selection of a strike zone area may indicate that the player should only swing at or react to balls pitched to the selected strike zone area(s). In this case, not every pitch is deemed hittable and the moving average algorithm may be modified as described further below.

The algorithm for calculating the moving average and adjusting the luminance of the pitched ball may be modified to produce the outputs shown in the following table for an intermediate player level.

| Intermediate Player Level Algorithm Table | | |
| --- | --- | --- |
| Designated Strike Zone Area | Player Swings at Ball | Pitch Affects Luminance Statistics |
| No | no | no |
| No | yes | yes |
| Yes | no | yes |
| Yes | yes | yes |

As shown in the intermediate algorithm table, when calculating the moving average, if the ball is pitched away from any selected strike zone area (i.e., the ball does not enter any player selected strike zone area) and the player does not swing at the ball, then the moving average is unaffected by that pitch. If the ball is pitched away from any selected strike zone area and the player does swing at the ball, then the miss may be counted in calculating the moving average. The last two rows illustrate cases when the ball is pitched in the selected strike zone area. In these two cases, the moving average may be calculated as normal. In other words, when the ball is in the designated strike zone areas, a pitched ball will be counted in calculating the moving average whether or not the player initiates a swing. In this manner, the player may be rewarded for recognizing balls pitched outside the designated strike zone areas when the player foregoes a swing.

Figure 16:
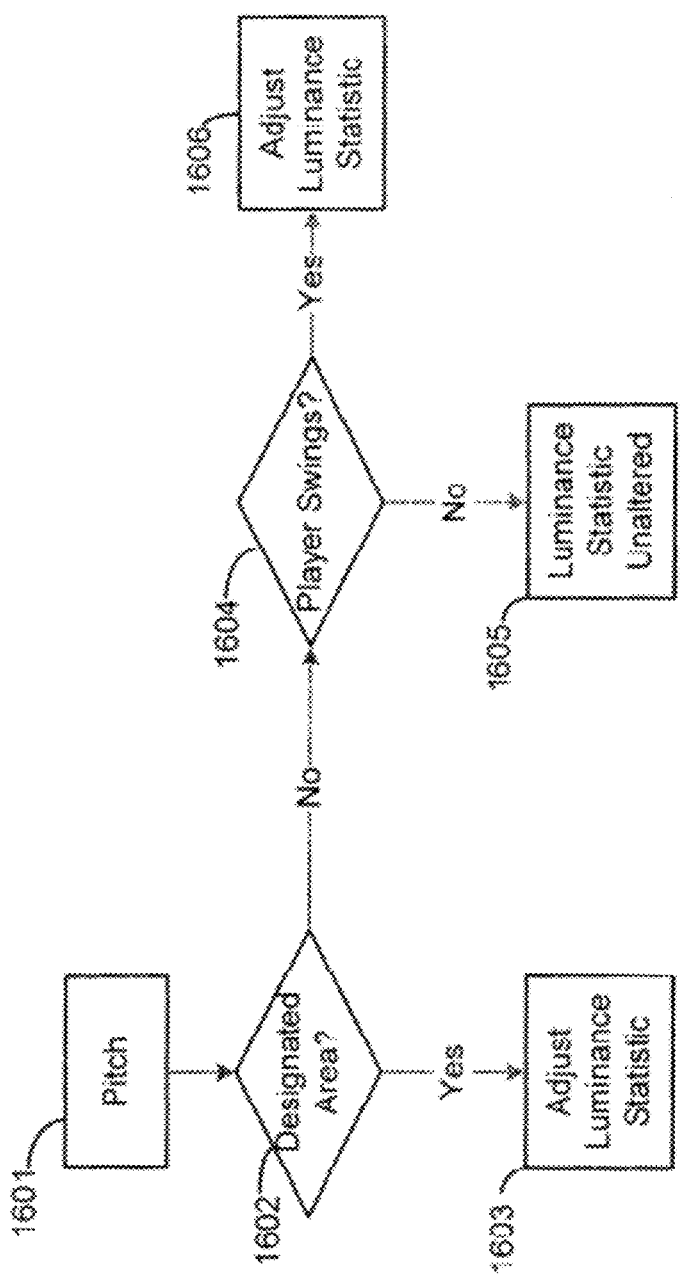
FIG. 16 illustrates a process of adjusting luminance for an intermediate player level.

FIG. 16 illustrates a process for implementing the intermediate player level algorithm. A pitch may be initiated at block 1601. A block 1602 may determine whether the pitch was made to a selected or designated strike zone area. If the pitch was made to the designated strike zone, then the luminance statistic may be affected. For example, in the embodiment illustrated in FIG. 13, the players swing will be recorded as a hit or miss and the luminance may be adjusted accordingly. If the ball was pitched outside any selected strike zone area, then block 1604 may determine whether the player initiated a swing. If the player did not swing at the ball pitched to a non-designated area, then the luminance statistic may be unaltered 1605. If the player did swing at the ball pitched to a non-designated area, then the luminance statistic may be adjusted based on whether the swing was a hit or miss 1606.

Figure 17:
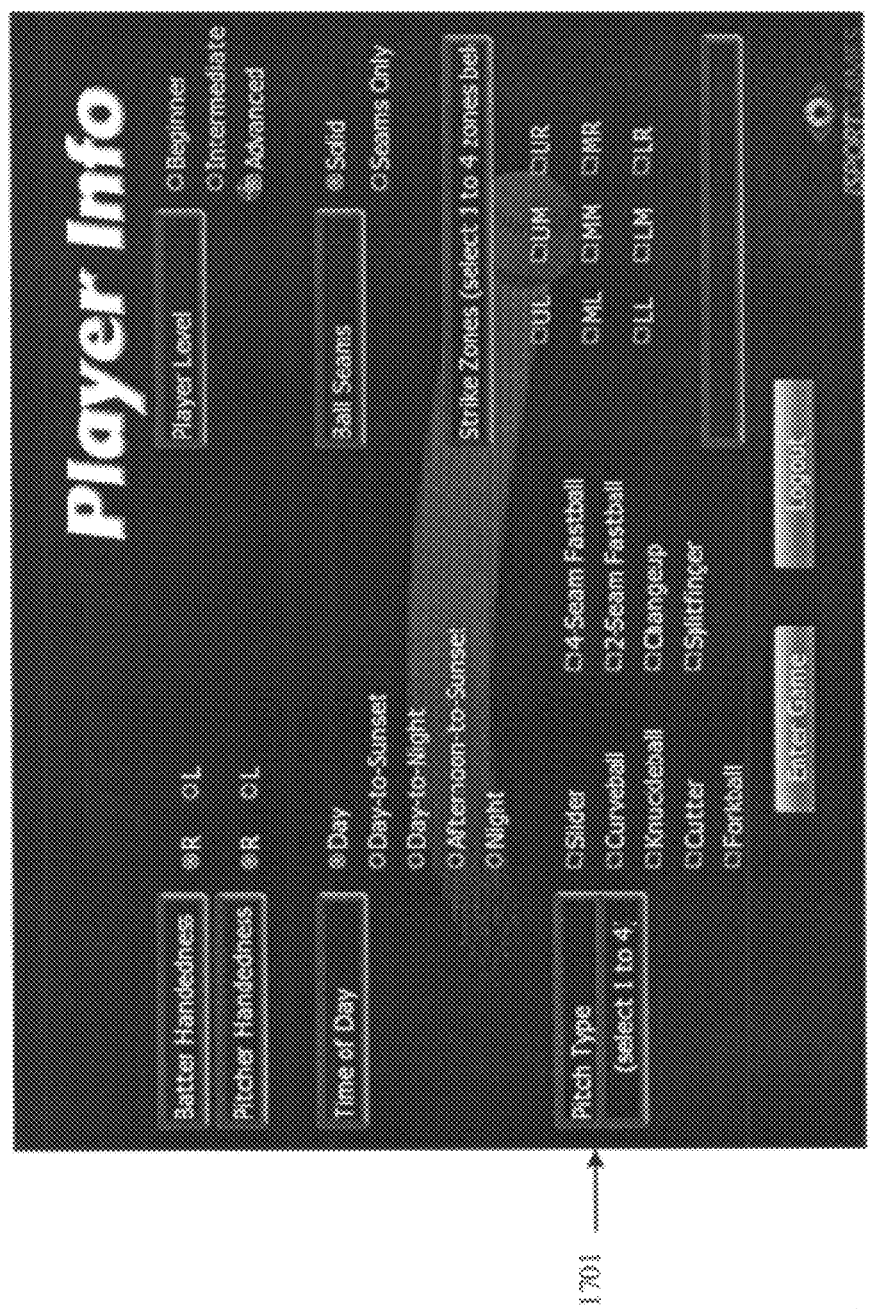
FIG. 17 illustrates a configuration screen for an advanced player level.

When an advanced player level is selected, a designated/selected pitch type parameter may be selectable in addition to selecting one or more strike zones. FIG. 17 illustrates an advanced level configuration screen. FIG. 17 illustrates several pitch types that may be selected from a listing 1701, including slider, curveball, knuckleball, cutter, forkball, 4-seam fastball, 2-seam fastball, changeup, and splitfinger. The pitch type listings 1701 may be expanded or reduced depending on a particular implementation. FIG. 17 illustrates that up to four different pitch types may be selected. The selection of a pitch type may indicate that pitches of that type may be selected for recognition by the batter or player. In this case, the player may aim to swing only at balls that are of the selected pitch type(s) in addition to being pitched in the selected strike zone area(s).

The algorithm for calculating the moving average and adjusting the luminance of the pitched ball may be modified to produce the outputs shown in the table below for an advanced player level.

| Advanced Player Level Algorithm Table | | | |
| --- | --- | --- | --- |
| Designated Strike Zone Areas | Designated Pitch Type | Player Swings at Ball | Pitch Affects Luminance Statistics |
| no | no | no | no |
| no | no | yes | yes |
| no | yes | no | no |
| no | yes | yes | yes |
| yes | no | no | no |
| yes | no | yes | yes |
| yes | yes | no | yes |
| yes | yes | yes | yes |

As shown in the advanced algorithm table above, when calculating the moving average, if the ball is pitched away from any selected strike zone area or the pitch is not one of the selected pitches, then a swing by the player is counted in calculating the moving average only if the player swings at the pitch, otherwise, the pitch is not counted in calculating the moving average. In other words, at the advanced player level, the player may be encouraged to recognize pitches that the player should not swing at and when foregoing a swing at non-designated pitches, the luminance is unaffected. As shown in the advanced algorithm table above, when the pitch is made to a selected strike zone area and the pitch type is one of the selected pitches, then the algorithm will always count the pitch (swing or no swing) in calculating the moving batting average.

Figure 18:
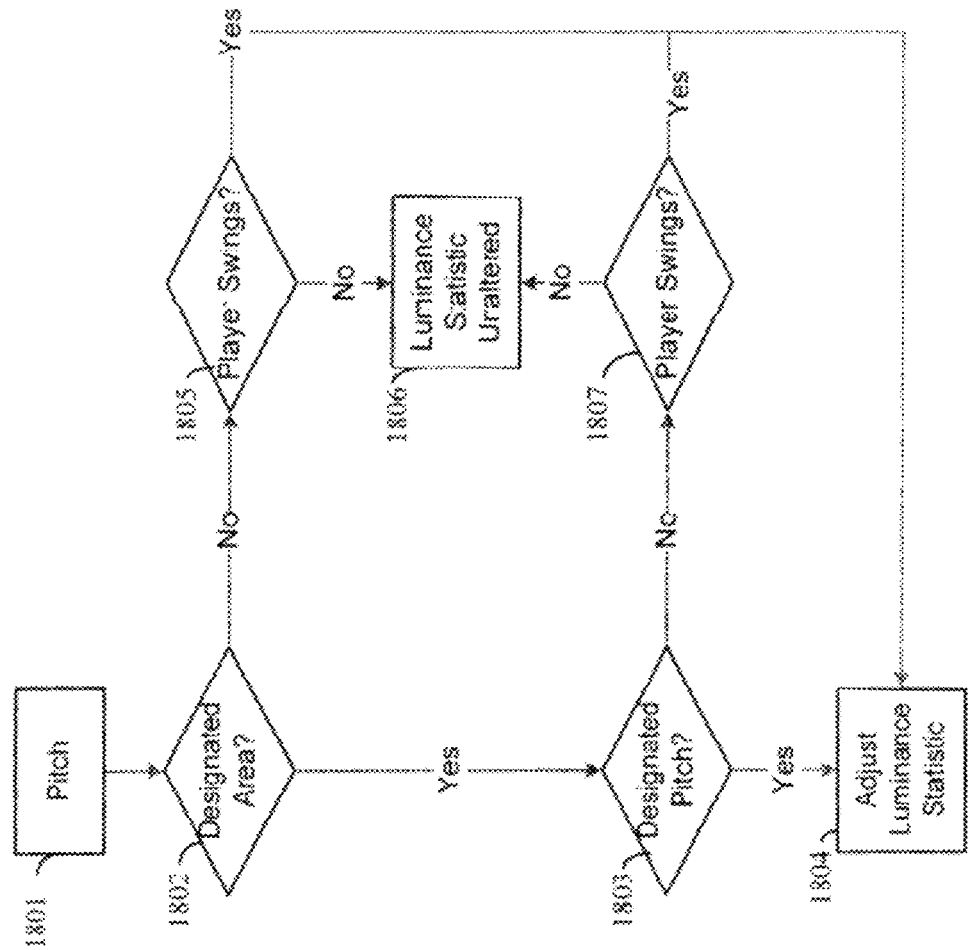
FIG. 18 illustrates a process of adjusting luminance for an advanced player level.

The advanced player algorithm may be further described by the process illustrated in FIG. 18. A pitch may be initiated at block 1801. A block 1802 may determine whether the pitch was made to a selected or designated strike zone area. If the pitch was made to the designated strike zone, then block 1803 may determine if the type of pitch was one of the selected or designated pitches. If both the type of pitch and placement of the pitch was designated, then the luminance algorithm may operate to count the swing as a hit or miss depending on the reaction of the player and the luminance may be adjusted as described in previous embodiments (e.g., based on thresholds). If the ball was pitched outside any selected strike zone area, then block 1805 may determine whether the player initiated a swing. If the player did not swing at the ball pitched to a non-designated area, then the luminance statistic may be unaltered 1806. If the player did swing at the ball pitched to a non-designated area, then the luminance statistic may be adjusted based on whether the swing was a hit or miss 1804. If the ball was not a selected pitched type, then block 1807 may determine whether the player initiated a swing. If the player did not swing at the non-designated pitch, then the luminance statistic may be unaltered 1806. If the player did swing at the non-designated pitch, then the luminance statistic may be adjusted based on whether the swing was a hit or miss 1804.

Other Embodiments

Figure 19:
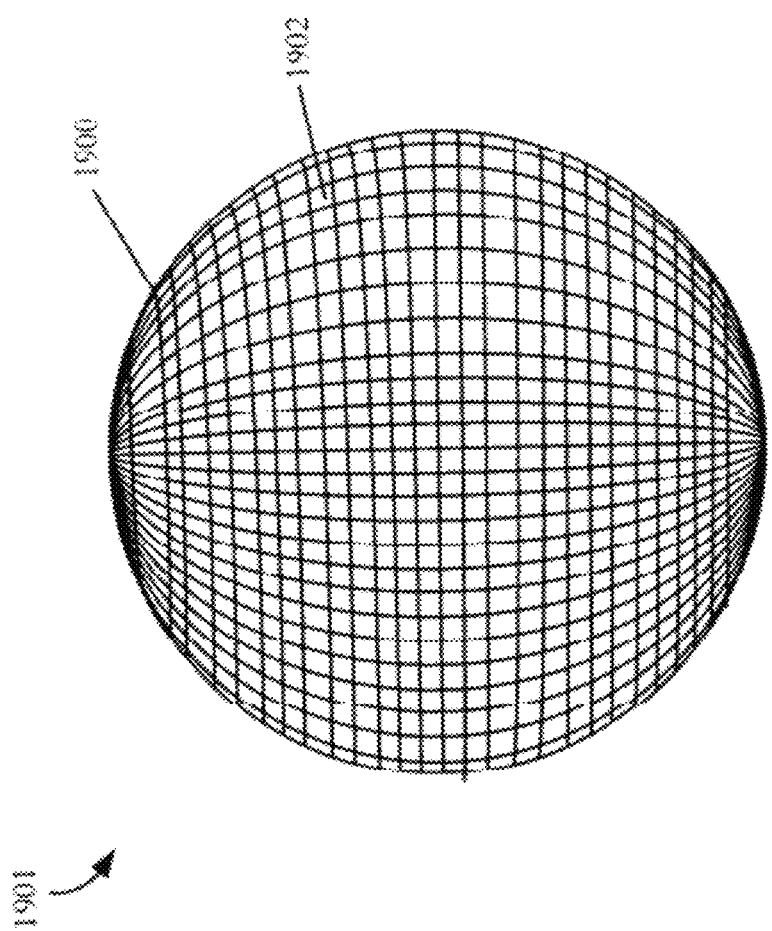
FIG. 19 illustrates an integrated ball display embodiment.

While a particular set of parameters for the baseball gaming embodiment is describe above, parameters may be changed and modified or new parameters added to the game embodiment while remaining within the scope of the present disclosure. For example, in a virtual gaming environment, a physical ball may be launched or pitched towards a user where the ball incorporates an electronic display on its outer surface. An integrated ball display embodiment is illustrated in FIG. 19. A display screen 1900 may be formed on the surface of a spherical object 1901. The display screen 1900 may comprise a plurality of pixel elements 1902 that are dispersed on the surface of the display screen. In one embodiment, the pixel elements are light emitting diodes (LED) and may be adapted to emit or reflect light at a particular intensity or color. A processor and power supply may be coupled to the display screen to allow certain images to be displayed on the surface of the spherical object. For example, in a baseball embodiment, the spherical object may be sized as a standard baseball with the display showing an image of a white surface and darker colored seams. Of course, other shapes and sizes may be used depending on the particular implementation. For example, if the game embodiment is applied to other sports, the object may be shaped and/or sized as a football, tennis ball, soccer ball, golf ball, or other piece of sporting equipment. It is further noted that the processor may be programmed with certain algorithms similar to those discussed above. In other words, the processor may make adjustments in the signals sent to the display based on the performance and experience of the player, by, for example, making the ball harder to see as the player's performance improves.

Figure 20:
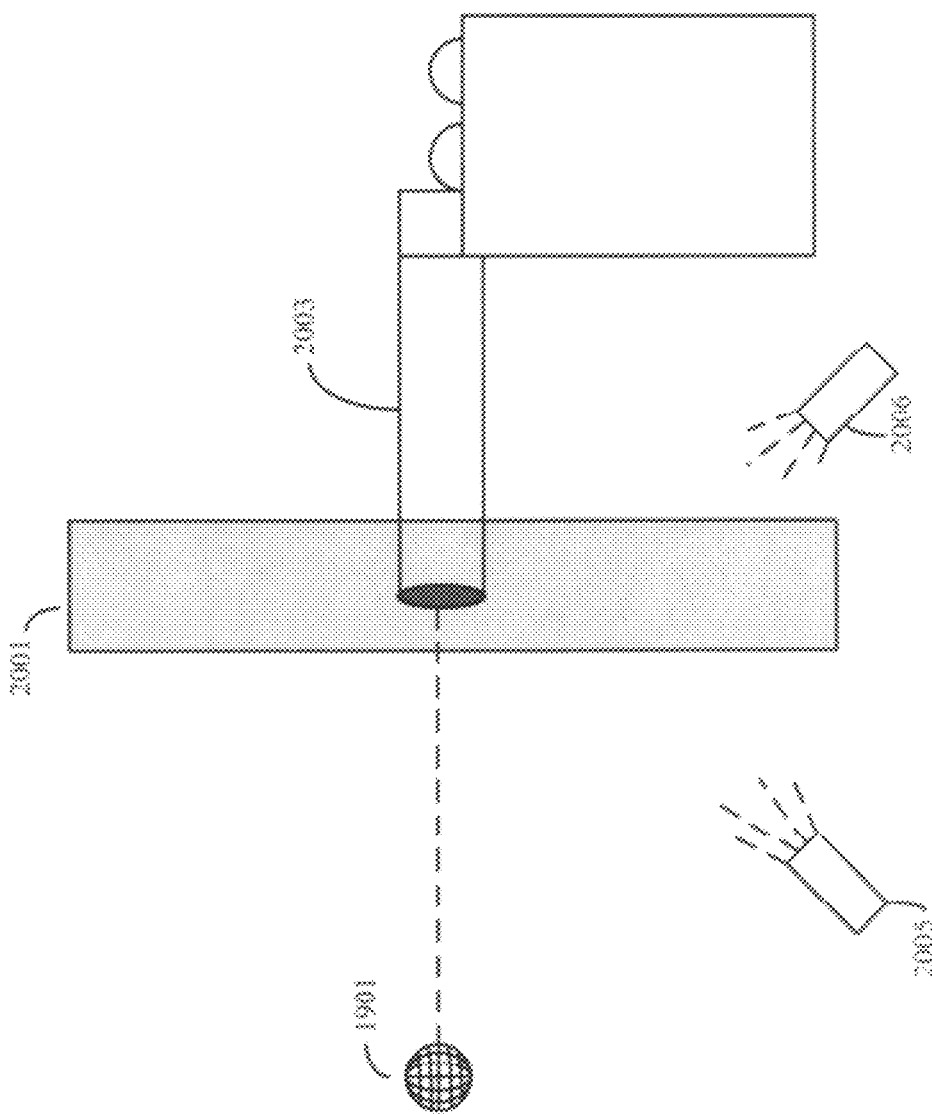
FIG. 20 illustrates a physical gaming embodiment in which the integrated ball display object of FIG. 19 is launched at a player from a screen representing a first field of view having constant intensity and color.

FIG. 20 illustrates that the ball may be pitched to the user from a screen representing a substantially constant first field of view at a first color and first intensity. For example, a screen 2001 may be disposed surrounding a mechanical ball launcher 2003 that launches the ball display object 1901. The color and intensity of the screen may be adjusted based on light projection devices 2005, 2006 (either one or both may be used). The ball display 1900 may be used to allow the ball 1901 to illuminate or emit a certain color at a certain intensity, thereby representing a second stimulus within the substantially constant first field of view, where the ball 1901 is either a different color from the first field of view 2001 and/or a different intensity from the first field of view 2001. The ball 1901 may be pitched in such a manner that its path remains within the first field of view. Alternatively, the screen may be sized to ensure that any balls launched will remain within the first field of view of the screen 2001.

Similar to the gaming embodiment described above, the ball display 1900 may also be adapted to change either its color or intensity during subsequent pitches in a game duration. Moreover, depending on the intended modification of a players visual processing profile, the ball appearance (e.g., color or intensity) may be modified during the flight of the ball 1901.

While a baseball game embodiment is described above, other gaming embodiments of the general invention may be used to modify a user's visual processing profile for a particular activity or sport. For example, the same physical baseball gaming environment described above may be adapted for a game of American football. For example, in one football gaming environment, instead of physically launching a baseball sized object towards a player, a football size object having an integrated display screen on its outer surface may be launched at a player. Similar to the virtual baseball gaming environment, the football object may be launched by a mechanical football launching device against a first screen that is adapted to display a substantially constant first field of view at a first color and first intensity. The football display may be adapted to display a second visual stimulus within the substantially constant first field of view, where the ball is either a different color from the first field of view and/or a different intensity from the first field of view. Similar to the baseball embodiment, both the display of the first field of view or the display of the football may be adjusted (e.g., intensity or color with respect to each other).

What is claimed:

1. A non-transitory computer readable storage medium comprising instructions for altering a retino-geniculo-cortical pathway of a user, the instructions for:
   displaying a first view set, the first view set comprising:
      a first field of view at a first color and a first intensity;
      a first stimulus, positioned at least partly within the first field of view, at a second color and a second intensity, wherein the second color is different from the first color or the second intensity is different from the first intensity;
   receiving a first input of the user responsive to the first view set;
   determining a characteristic for a second view set, the determining comprising:
      assessing whether a parameter of the first input of the user meets a first parameter criteria, wherein the first parameter criteria is not met if the first input of the user is not received within an allowed period of time;
      modifying a first value if the first parameter criteria is met;
      modifying a second value if the first parameter criteria is not met;
      calculating a first user rating based on the first value and the second value;
      comparing the first user rating to a user rating threshold;
      selecting the characteristic of the second view set based on the comparison of the first user rating to the user rating threshold.

2. The non-transitory computer readable storage medium claim 1, further comprising a processor for executing the instructions, light emitting diode display, and a power supply, wherein the computing system is integrated into a piece of sporting equipment.

3. The non-transitory computer readable storage medium of claim 1, the instructions further comprising:
   displaying the second view set after determining the characteristic for the second view set, the second view set comprising:
      a second field of view at a third color and a third intensity;
      a second stimulus, positioned at least partly within the second field of view, at a fourth color and a fourth intensity, wherein the fourth color is different from the third color or the fourth intensity is different from the third intensity;
   receiving a second input of the user responsive to the second view set;
   determining a characteristic for a third view set, the determining comprising:
      assessing whether a parameter of the second input of the user meets a second parameter criteria, wherein the second parameter criteria is not met if the second input of the user is not received within an allowed period of time;
      modifying the first value if the second parameter criteria is met;
      modifying the second value if the second parameter criteria is not met;
      calculating a second user rating based on the first value and the second value; comparing the second user rating to a second user rating threshold;
      selecting the characteristic of the third view set based on the comparison of the second user rating to the second user rating threshold.

4. The non-transitory computer readable storage medium of claim 1, wherein the characteristic of the second view set is selected from the group consisting of an intensity of a second stimulus of the second view set, a color of the second stimulus of the second view set, a position of the second stimulus of the second view set, a motion of the second stimulus of the second view set, a timing of the second stimulus of the second view set, and a flicker rate of the second stimulus of the second view set.

5. The non-transitory computer readable storage medium of claim 1, wherein the first stimulus models a movement of an object either toward or away from the user.

6. The non-transitory computer readable storage medium of claim 1, wherein the first color and the second color are selected based on a visual processing profile previously determined for the user.

7. The non-transitory computer readable storage medium of claim 6, the instructions further comprising comparing the user's visual processing profile to a predetermined visual processing profile to determine a variance from the predetermined visual processing profile, and selecting the first color and the second color based on the determined variance.

8. The non-transitory computer readable storage medium of claim 1, wherein the first color and the second color are selected based on a ratio of levels of retinal ganglion function for a plurality of magnocellular cells and a plurality of non-magnocellular cells.

9. The non-transitory computer readable storage medium of claim 1, further comprising repeating the instructions for a predetermined time period.

10. The non-transitory computer readable storage medium of claim 1, the instructions further comprising: selecting a position of a second stimulus of the second view set based on the comparison of the first user rating to the user rating threshold.

11. The non-transitory computer readable storage medium of claim 1, wherein the first view set is a graphical simulation of a physical activity.

12. The non-transitory computer readable storage medium of claim 11, the instructions further comprising: displaying instructions for the user to perform the physical activity within a set period of time.

13. The non-transitory computer readable storage medium of claim 11, wherein the physical activity is baseball, the first field of view models a portion of the perspective of a batter, the first stimulus models a movement of a pitched baseball, the parameter of the first input of the user is based at least in part on an input timing, the first parameter criteria is based at least in part on an input timing, the first value is a counter of hits, the second value is a counter of misses, and the first user rating is a batting average.

14. The non-transitory computer readable storage medium of claim 13, wherein the first stimulus may model the movement of a pitched baseball that is within a designated strike zone area or not within a designated strike zone area.

15. The non-transitory computer readable storage medium of claim 13, wherein the first input of the user is not received within the allowed period of time, and the determining the characteristic for the second view set further comprises:
assessing whether the first stimulus modeled the movement of the pitched baseball that is not within a designated strike zone area; wherein modifying the counter of misses does not occur if the movement of the pitched baseball is not within a designated strike zone area.

16. The non-transitory computer readable storage medium of claim 13, the instructions further comprising receiving a user selection of the designated strike zone area, prior to displaying the first view set.

17. The non-transitory computer readable storage medium of claim 13, wherein the first view set further comprises modeling a pitcher, wherein the pitcher may be a right-handed pitcher or a left-handed pitcher, wherein the first stimulus models a movement of the baseball either toward or away from the user, and wherein the movement of the baseball is based on whether the pitcher is right-handed or left-handed.

18. The non-transitory computer readable storage medium of claim 13, wherein the movement of the pitched baseball models a pitch type selected from the group consisting of a slider, a curveball, a knuckleball, a cutter, a forkball, a 4-seam fastball, a 2-seam fastball, a changeup, and a split-finger.

19. The non-transitory computer readable storage medium of claim 18, wherein the first input of the user is not received within the allowed period of time, and the determining the characteristic for the second view set further comprises:
assessing whether the first stimulus modeled the movement of a pitched baseball that does not match the selected pitch type; wherein modifying the counter of misses does not occur if the movement of the pitched baseball does not match the selected pitch type.

20. The non-transitory computer readable storage medium of claim 18, the instructions further comprising receiving a user selection of a pitch type, prior to displaying the first view set.

* * * * *